(12) United States Patent
Al-Ali

(10) Patent No.: US 9,775,570 B2
(45) Date of Patent: Oct. 3, 2017

(54) ADAPTIVE ALARM SYSTEM

(71) Applicant: MASIMO Corporation, Irvine, CA (US)

(72) Inventor: Ammar Al-Ali, San Juan Capistrano, CA (US)

(73) Assignee: Masimo Corporation, Irvine, CA (US)

( * ) Notice: Subject to any disclaimer, the term of this patent is extended or adjusted under 35 U.S.C. 154(b) by 0 days.

(21) Appl. No.: 15/583,718

(22) Filed: May 1, 2017

(65) Prior Publication Data

US 2017/0231537 A1   Aug. 17, 2017

Related U.S. Application Data

(63) Continuation of application No. 13/037,184, filed on Feb. 28, 2011.

(60) Provisional application No. 61/309,419, filed on Mar. 1, 2010, provisional application No. 61/328,630, filed on Apr. 27, 2010.

(51) Int. Cl.
*A61B 5/00* (2006.01)
*A61B 5/1455* (2006.01)

(52) U.S. Cl.
CPC ............ *A61B 5/746* (2013.01); *A61B 5/1455* (2013.01); *A61B 5/14552* (2013.01); *A61B 5/74* (2013.01)

(58) Field of Classification Search
CPC . A61B 5/0205; A61B 5/1455; A61B 5/14551; A61B 5/14552; A61B 5/72; A61B 5/74; A61B 5/746
See application file for complete search history.

(56) References Cited

U.S. PATENT DOCUMENTS 4,960,128 A   10/1990   Gordon et al.
4,964,408 A   10/1990   Hink et al.
(Continued)

FOREIGN PATENT DOCUMENTS

WO   WO 03/007815    1/2003
WO   WO 03/028549    4/2003
WO   WO 2009/093159  7/2009

OTHER PUBLICATIONS

US 9,579,050, 02/2017, Al-Ali (withdrawn)
(Continued)

*Primary Examiner* — Eric Winakur
*Assistant Examiner* — Chu Chuan (JJ) Liu
(74) *Attorney, Agent, or Firm* — Knobbe Martens Olson & Bear, LLP

(57) ABSTRACT

Systems and electronic processes for reducing electronic alarms in a medical patient monitoring system. For example, a system for reducing electronic alarms can include an optical sensor and one or more hardware processors in electronic communication with the optical sensor. The one or more hardware processors can be programmed to measure oxygen saturation values of a patient over a first period of time, determine if at least one oxygen saturation value obtained over the first period of time exceeds a first alarm threshold, determine whether a first alarm should be triggered based on the determination that the at least one oxygen saturation value obtained over the first period of time exceeds the first alarm threshold, determine a second alarm threshold to be applied during a second period of time subsequent to the first period of time, the second alarm threshold replacing the first alarm threshold.

18 Claims, 14 Drawing Sheets

(56) References Cited

U.S. PATENT DOCUMENTS

| | | |
|---|---|---|
| 5,041,187 A | 8/1991 | Hink et al. |
| 5,069,213 A | 12/1991 | Polczynski |
| 5,163,438 A | 11/1992 | Gordon et al. |
| 5,285,782 A | 2/1994 | Prosser |
| 5,319,355 A | 6/1994 | Russek |
| 5,337,744 A | 8/1994 | Branigan |
| 5,341,805 A | 8/1994 | Stavridi et al. |
| D353,195 S | 12/1994 | Savage et al. |
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,464,012 A | 11/1995 | Falcone |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,685,299 A | 11/1997 | Diab et al. |
| D393,830 S | 4/1998 | Tobler et al. |
| 5,743,262 A | 4/1998 | Lepper, Jr. et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,027,452 A | 2/2000 | Flaherty et al. |
| 6,036,642 A | 3/2000 | Diab et al. |
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,661 B1 | 6/2001 | Schluess et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,639,668 B1 | 10/2003 | Trepagnier |
| 6,640,116 B2 | 10/2003 | Diab |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,754,516 B2 | 6/2004 | Manheimer |
| 6,760,607 B2 | 7/2004 | Al-Ali |
| 6,770,028 B1 | 8/2004 | Ali et al. |
| 6,771,994 B2 | 8/2004 | Kiani et al. |
| 6,792,300 B1 | 9/2004 | Diab et al. |
| 6,813,511 B2 | 11/2004 | Diab et al. |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,898,452 B2 | 5/2005 | Al-Ali et al. |

(56) References Cited

U.S. PATENT DOCUMENTS

| | | | |
|---|---|---|---|
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,993,371 B2 | 1/2006 | Kiani et al. |
| 6,996,427 B2 | 2/2006 | Ali et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,067,893 B2 | 6/2006 | Mills et al. |
| 7,096,052 B2 | 8/2006 | Mason et al. |
| 7,096,054 B2 | 8/2006 | Abdul-Hafiz et al. |
| 7,132,641 B2 | 11/2006 | Schulz et al. |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al-Ali et al. |
| 7,377,899 B2 | 5/2008 | Weber et al. |
| 7,383,070 B2 | 6/2008 | Diab et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,526,328 B2 | 4/2009 | Diab et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,596,398 B2 | 9/2009 | Al-Ali et al. |
| 7,618,375 B2 | 11/2009 | Flaherty |
| D606,659 S | 12/2009 | Kiani et al. |
| 7,647,083 B2 | 1/2010 | Al-Ali et al. |
| D609,193 S | 2/2010 | Al-Ali et al. |
| D614,305 S | 4/2010 | Al-Ali et al. |
| RE41,317 E | 5/2010 | Parker |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |

(56) References Cited

U.S. PATENT DOCUMENTS

| | | |
|---|---|---|
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-Ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | Macneish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |

(56) References Cited

U.S. PATENT DOCUMENTS

| | | |
|---|---|---|
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,693 B2 | 4/2017 | Diab |
| 2007/0156031 A1* | 7/2007 | Sullivan ............ A61B 5/7282 600/300 |
| 2007/0282478 A1 | 12/2007 | Al-Ali et al. |
| 2008/0157980 A1 | 7/2008 | Sachanandani et al. |
| 2009/0210163 A1 | 8/2009 | Ochs et al. |
| 2009/0247848 A1* | 10/2009 | Baker, Jr. .......... A61B 5/14551 600/323 |
| 2009/0247984 A1 | 10/2009 | Lamego et al. |
| 2009/0275813 A1 | 11/2009 | Davis |
| 2009/0275844 A1 | 11/2009 | Al-Ali |
| 2009/0299157 A1 | 12/2009 | Telfort et al. |
| 2010/0004518 A1 | 1/2010 | Vo et al. |
| 2010/0030040 A1 | 2/2010 | Poeze et al. |
| 2010/0261979 A1 | 10/2010 | Kiani |
| 2011/0001605 A1 | 1/2011 | Kiani et al. |
| 2011/0082711 A1 | 4/2011 | Poeze et al. |
| 2011/0105854 A1 | 5/2011 | Kiani et al. |
| 2011/0125060 A1 | 5/2011 | Telfort et al. |
| 2011/0208015 A1 | 8/2011 | Welch et al. |
| 2011/0209915 A1 | 9/2011 | Telfort et al. |
| 2011/0213212 A1 | 9/2011 | Al-Ali |
| 2011/0230733 A1 | 9/2011 | Al-Ali |
| 2011/0237911 A1 | 9/2011 | Lamego et al. |
| 2011/0237969 A1 | 9/2011 | Eckerbom et al. |
| 2011/0288383 A1 | 11/2011 | Diab |
| 2012/0041316 A1 | 2/2012 | Al Ali et al. |
| 2012/0046557 A1 | 2/2012 | Kiani |
| 2012/0059267 A1 | 3/2012 | Lamego et al. |
| 2012/0088984 A1 | 4/2012 | Al-Ali et al. |
| 2012/0116175 A1 | 5/2012 | Al-Ali et al. |
| 2012/0165629 A1 | 6/2012 | Merritt et al. |
| 2012/0179006 A1 | 7/2012 | Jansen et al. |
| 2012/0209082 A1 | 8/2012 | Al-Ali |
| 2012/0209084 A1 | 8/2012 | Olsen et al. |
| 2012/0227739 A1 | 9/2012 | Kiani |
| 2012/0265039 A1 | 10/2012 | Kiani |
| 2012/0283524 A1 | 11/2012 | Kiani et al. |
| 2012/0286955 A1 | 11/2012 | Welch et al. |
| 2012/0296178 A1 | 11/2012 | Lamego et al. |
| 2012/0319816 A1 | 12/2012 | Al-Ali |
| 2012/0330112 A1 | 12/2012 | Lamego et al. |
| 2013/0023775 A1 | 1/2013 | Lamego et al. |
| 2013/0041591 A1 | 2/2013 | Lamego |
| 2013/0045685 A1 | 2/2013 | Kiani |
| 2013/0046204 A1 | 2/2013 | Lamego et al. |
| 2013/0060108 A1 | 3/2013 | Schurman et al. |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0109935 A1 | 5/2013 | Al-Ali et al. |
| 2013/0162433 A1 | 6/2013 | Muhsin et al. |
| 2013/0190581 A1 | 7/2013 | Al-Ali et al. |
| 2013/0197328 A1 | 8/2013 | Diab et al. |
| 2013/0211214 A1 | 8/2013 | Olsen |
| 2013/0243021 A1 | 9/2013 | Siskavich |
| 2013/0253334 A1 | 9/2013 | Al-Ali et al. |
| 2013/0267804 A1 | 10/2013 | Al-Ali |
| 2013/0274571 A1 | 10/2013 | Diab et al. |
| 2013/0274572 A1 | 10/2013 | Al-Ali et al. |
| 2013/0296672 A1 | 11/2013 | O'Neil et al. |
| 2013/0296713 A1 | 11/2013 | Al-Ali et al. |
| 2013/0317370 A1 | 11/2013 | Dalvi et al. |
| 2013/0324808 A1 | 12/2013 | Al-Ali et al. |
| 2013/0331660 A1 | 12/2013 | Al-Ali et al. |
| 2013/0331670 A1 | 12/2013 | Kiani |
| 2013/0338461 A1 | 12/2013 | Lamego et al. |
| 2014/0012100 A1 | 1/2014 | Al-Ali et al. |

(56) References Cited

U.S. PATENT DOCUMENTS

| | | |
|---|---|---|
| 2014/0025306 A1 | 1/2014 | Weber et al. |
| 2014/0034353 A1 | 2/2014 | Al-Ali et al. |
| 2014/0051952 A1 | 2/2014 | Reichgott et al. |
| 2014/0051953 A1 | 2/2014 | Lamego et al. |
| 2014/0051954 A1 | 2/2014 | Al-Ali et al. |
| 2014/0058230 A1 | 2/2014 | Abdul-Hafiz et al. |
| 2014/0066783 A1 | 3/2014 | Kiani et al. |
| 2014/0077956 A1 | 3/2014 | Sampath et al. |
| 2014/0081100 A1 | 3/2014 | Muhsin et al. |
| 2014/0081175 A1 | 3/2014 | Telfort |
| 2014/0094667 A1 | 4/2014 | Schurman et al. |
| 2014/0100434 A1 | 4/2014 | Diab et al. |
| 2014/0114199 A1 | 4/2014 | Lamego et al. |
| 2014/0120564 A1 | 5/2014 | Workman et al. |
| 2014/0121482 A1 | 5/2014 | Merritt et al. |
| 2014/0121483 A1 | 5/2014 | Kiani |
| 2014/0125495 A1 | 5/2014 | Al-Ali |
| 2014/0127137 A1 | 5/2014 | Bellott et al. |
| 2014/0128696 A1 | 5/2014 | Al-Ali |
| 2014/0128699 A1 | 5/2014 | Al-Ali et al. |
| 2014/0129702 A1 | 5/2014 | Lamego et al. |
| 2014/0135588 A1 | 5/2014 | Al-Ali et al. |
| 2014/0142401 A1 | 5/2014 | Al-Ali et al. |
| 2014/0142402 A1 | 5/2014 | Al-Ali et al. |
| 2014/0163344 A1 | 6/2014 | Al-Ali |
| 2014/0163402 A1 | 6/2014 | Lamego et al. |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0187973 A1 | 7/2014 | Brown et al. |
| 2014/0194709 A1 | 7/2014 | Al-Ali et al. |
| 2014/0194711 A1 | 7/2014 | Al-Ali |
| 2014/0194766 A1 | 7/2014 | Al-Ali et al. |
| 2014/0200420 A1 | 7/2014 | Al-Ali |
| 2014/0200422 A1 | 7/2014 | Weber et al. |
| 2014/0206963 A1 | 7/2014 | Al-Ali |
| 2014/0213864 A1 | 7/2014 | Abdul-Hafiz et al. |
| 2014/0243627 A1 | 8/2014 | Diab et al. |
| 2014/0266790 A1 | 9/2014 | Al-Ali et al. |
| 2014/0275808 A1 | 9/2014 | Poeze et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0275881 A1 | 9/2014 | Lamego et al. |
| 2014/0276115 A1 | 9/2014 | Dalvi et al. |
| 2014/0288400 A1 | 9/2014 | Diab et al. |
| 2014/0296664 A1 | 10/2014 | Bruinsma et al. |
| 2014/0303520 A1 | 10/2014 | Telfort et al. |
| 2014/0309506 A1 | 10/2014 | Lamego et al. |
| 2014/0309559 A1 | 10/2014 | Telfort et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0330099 A1 | 11/2014 | Al-Ali et al. |
| 2014/0333440 A1 | 11/2014 | Kiani |
| 2014/0336481 A1 | 11/2014 | Shakespeare et al. |
| 2014/0343436 A1 | 11/2014 | Kiani |
| 2015/0005600 A1 | 1/2015 | Blank et al. |
| 2015/0011907 A1 | 1/2015 | Purdon et al. |
| 2015/0012231 A1 | 1/2015 | Poeze et al. |
| 2015/0018650 A1 | 1/2015 | Al-Ali et al. |
| 2015/0025406 A1 | 1/2015 | Al-Ali |
| 2015/0032029 A1 | 1/2015 | Al-Ali et al. |
| 2015/0038859 A1 | 2/2015 | Dalvi et al. |
| 2015/0045637 A1 | 2/2015 | Dalvi |
| 2015/0051462 A1 | 2/2015 | Olsen |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0097701 A1 | 4/2015 | Al-Ali et al. |
| 2015/0099950 A1 | 4/2015 | Al-Ali et al. |
| 2015/0099951 A1 | 4/2015 | Al-Ali et al. |
| 2015/0099955 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0116076 A1 | 4/2015 | Al-Ali et al. |
| 2015/0126830 A1 | 5/2015 | Schurman et al. |
| 2015/0133755 A1 | 5/2015 | Smith et al. |
| 2015/0141781 A1 | 5/2015 | Weber et al. |
| 2015/0165312 A1 | 6/2015 | Kiani |
| 2015/0196237 A1 | 7/2015 | Lamego |
| 2015/0216459 A1 | 8/2015 | Al-Ali et al. |
| 2015/0230755 A1 | 8/2015 | Al-Ali et al. |
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0351704 A1 | 12/2015 | Kiani et al. |
| 2015/0359429 A1 | 12/2015 | Al-Ali et al. |
| 2015/0366472 A1 | 12/2015 | Kiani |
| 2015/0366507 A1 | 12/2015 | Blank |
| 2015/0374298 A1 | 12/2015 | Al-Ali et al. |
| 2015/0380875 A1 | 12/2015 | Coverston et al. |
| 2016/0000362 A1 | 1/2016 | Diab et al. |
| 2016/0007930 A1 | 1/2016 | Weber et al. |
| 2016/0029932 A1 | 2/2016 | Al-Ali |
| 2016/0045118 A1 | 2/2016 | Kiani |
| 2016/0051205 A1 | 2/2016 | Al-Ali et al. |
| 2016/0058338 A1 | 3/2016 | Schurman et al. |
| 2016/0058347 A1 | 3/2016 | Reichgott et al. |
| 2016/0066823 A1 | 3/2016 | Al-Ali et al. |
| 2016/0066824 A1 | 3/2016 | Al-Ali et al. |
| 2016/0066879 A1 | 3/2016 | Telfort et al. |
| 2016/0072429 A1 | 3/2016 | Kiani et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0113527 A1 | 4/2016 | Al-Ali et al. |
| 2016/0143548 A1 | 5/2016 | Al-Ali |
| 2016/0166182 A1 | 6/2016 | Al-Ali et al. |
| 2016/0166183 A1 | 6/2016 | Poeze et al. |
| 2016/0166188 A1 | 6/2016 | Bruinsma et al. |
| 2016/0166210 A1 | 6/2016 | Al-Ali |
| 2016/0192869 A1 | 7/2016 | Kiani et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324486 A1 | 11/2016 | Al-Ali et al. |
| 2016/0324488 A1 | 11/2016 | Olsen |
| 2016/0327984 A1 | 11/2016 | Al-Ali et al. |
| 2016/0328528 A1 | 11/2016 | Al-Ali et al. |
| 2016/0331332 A1 | 11/2016 | Al-Ali |
| 2016/0367173 A1 | 12/2016 | Dalvi et al. |
| 2017/0007134 A1 | 1/2017 | Al-Ali et al. |
| 2017/0007190 A1 | 1/2017 | Al-Ali et al. |
| 2017/0007198 A1 | 1/2017 | Al-Ali et al. |
| 2017/0014084 A1 | 1/2017 | Al-Ali et al. |
| 2017/0021099 A1 | 1/2017 | Al-Ali et al. |
| 2017/0027456 A1 | 2/2017 | Kinast et al. |
| 2017/0042488 A1 | 2/2017 | Muhsin |
| 2017/0055847 A1 | 3/2017 | Kiani et al. |
| 2017/0055851 A1 | 3/2017 | Al-Ali |
| 2017/0055882 A1 | 3/2017 | Al-Ali et al. |
| 2017/0055887 A1 | 3/2017 | Al-Ali |

(56) References Cited

U.S. PATENT DOCUMENTS

2017/0055896 A1   3/2017   Al-Ali et al.
2017/0079594 A1   3/2017   Telfort et al.
2017/0086723 A1   3/2017   Al-Ali et al.

OTHER PUBLICATIONS

US 8,845,543, Diab et al. (withdrawn)
Coetzee, et al., "Noise-Resistant Pulse Oximetry Using a Synthetic Reference Signal," IEEE Transactions on Biomedical Engineering, IEEE Service Center, Piscataway, NJ, vol. 47, No. 8, dated Aug. 1, 2000.
Invitation to Pay Additional Fees document, including communication relating to the results of a partial Search Report issued in related application No. PCT/US2011/026545, dated Jun. 22, 2011, in 5 pages.
"Propaq Encore Vital Signs Monitor: Reference Guide," Welch Allyn, Inc., 2009 in 144 pages.

\* cited by examiner

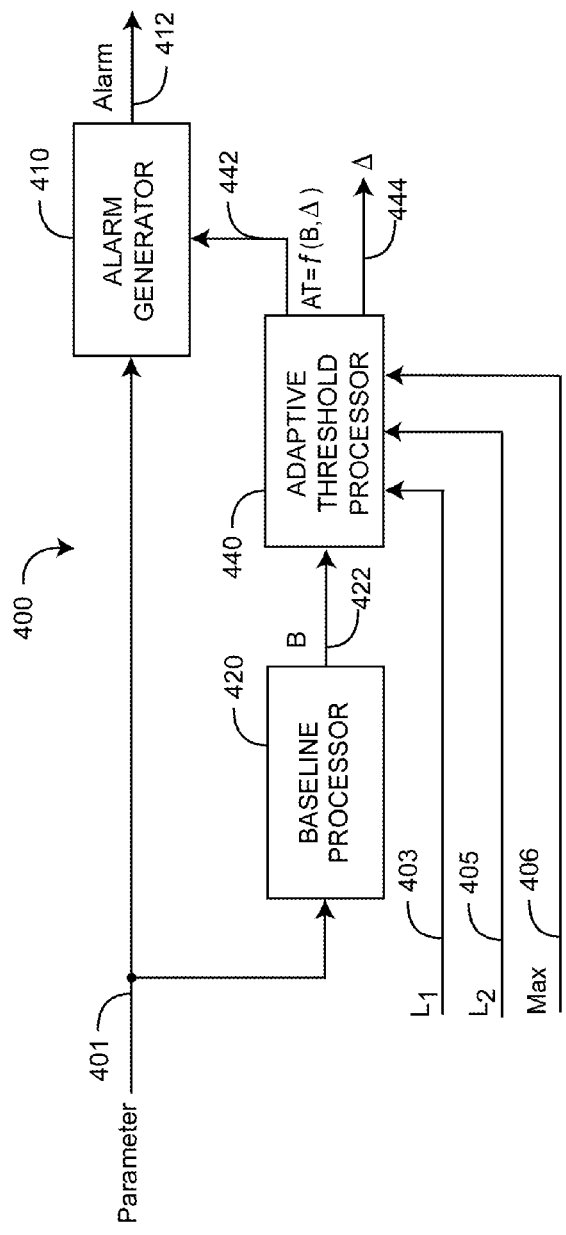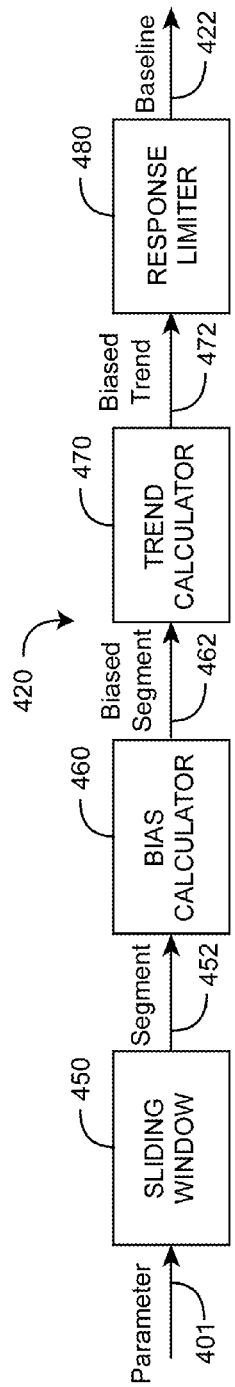
FIG. 4A
FIG. 4B

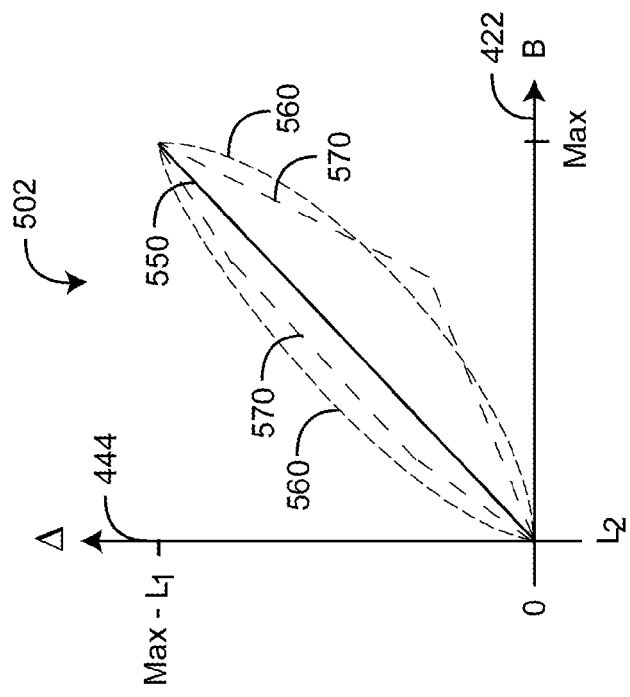
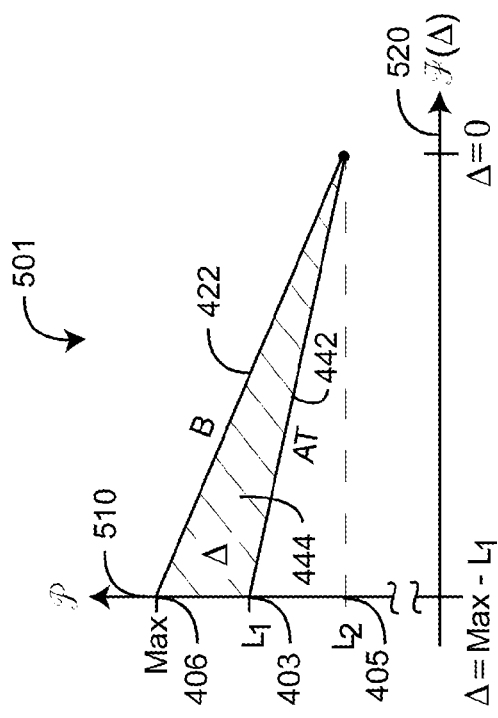
FIG. 5B
FIG. 5A

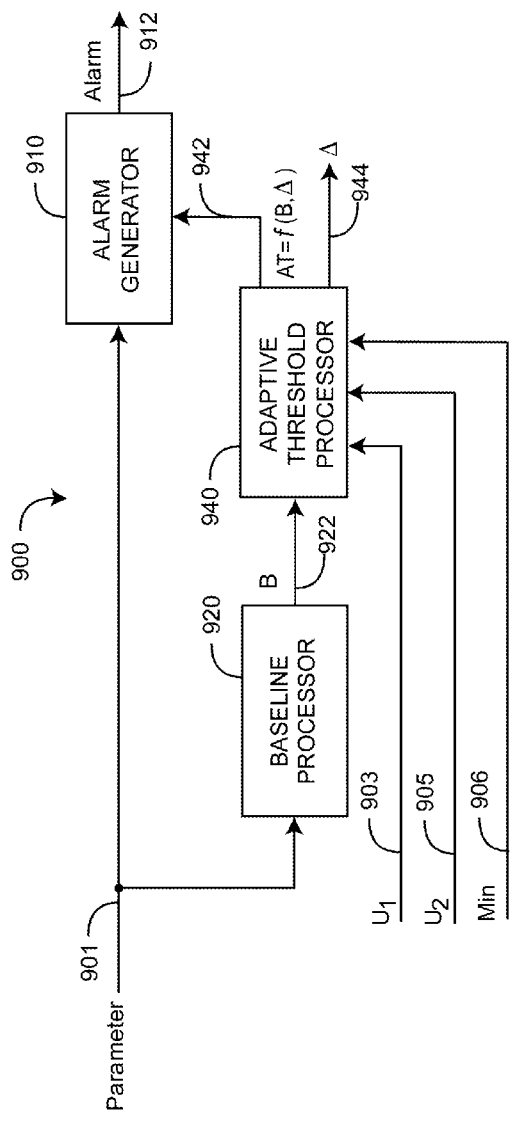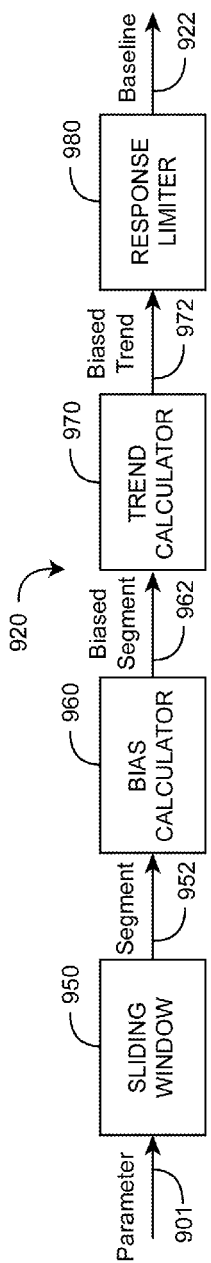
FIG. 9A
FIG. 9B

US 9,775,570 B2

ADAPTIVE ALARM SYSTEM

PRIORITY CLAIM TO RELATED PROVISIONAL APPLICATIONS

The present application claims priority benefit under 35 U.S.C. §119(e) to U.S. patent application Ser. No. 13/037,184, filed Feb. 18, 2011 titled Adaptive Alarm System; Provisional Patent Application Ser. No. 61/309,419, filed Mar. 1, 2010 titled Adaptive Threshold Alarm System; and U.S. Provisional Patent Application Ser. No. 61/328,630, filed Apr. 27, 2010 titled Adaptive Alarm System; all of the above-cited provisional patent applications are hereby incorporated by reference herein.

BACKGROUND OF THE INVENTION

Pulse oximetry systems for measuring constituents of circulating blood have gained rapid acceptance in a wide variety of medical applications, including surgical wards, intensive care and neonatal units, general wards, home care, physical training, and virtually all types of monitoring scenarios. A pulse oximetry system generally includes an optical sensor applied to a patient, a monitor for processing sensor signals and displaying results and a patient cable electrically interconnecting the sensor and the monitor. A pulse oximetry sensor has light emitting diodes (LEDs), typically one emitting a red wavelength and one emitting an infrared (IR) wavelength, and a photodiode detector. The emitters and detector are typically attached to a finger, and the patient cable transmits drive signals to these emitters from the monitor. The emitters respond to the drive signals to transmit light into the fleshy fingertip tissue. The detector generates a signal responsive to the emitted light after attenuation by pulsatile blood flow within the fingertip. The patient cable transmits the detector signal to the monitor, which processes the signal to provide a numerical readout of physiological parameters such as oxygen saturation ($SpO_2$) and pulse rate.

SUMMARY OF THE INVENTION

Conventional pulse oximetry assumes that arterial blood is the only pulsatile blood flow in the measurement site. During patient motion, venous blood also moves, which causes errors in conventional pulse oximetry. Advanced pulse oximetry processes the venous blood signal so as to report true arterial oxygen saturation and pulse rate under conditions of patient movement. Advanced pulse oximetry also functions under conditions of low perfusion (small signal amplitude), intense ambient light (artificial or sunlight) and electrosurgical instrument interference, which are scenarios where conventional pulse oximetry tends to fail.

Advanced pulse oximetry is described in at least U.S. Pat. Nos. 6,770,028; 6,658,276; 6,157,850; 6,002,952; 5,769,785 and 5,758,644, which are assigned to Masimo Corporation ("Masimo") of Irvine, Calif. and are incorporated by reference herein. Corresponding low noise optical sensors are disclosed in at least U.S. Pat. Nos. 6,985,764; 6,813,511; 6,792,300; 6,256,523; 6,088,607; 5,782,757 and 5,638,818, which are also assigned to Masimo and are also incorporated by reference herein. Advanced pulse oximetry systems including Masimo SET® low noise optical sensors and read through motion pulse oximetry monitors for measuring $SpO_2$, pulse rate (PR) and perfusion index (PI) are available from Masimo. Optical sensors include any of Masimo LNOP®, LNCS®, SofTouch™ and Blue™ adhesive or reusable sensors. Pulse oximetry monitors include any of Masimo Rad-8®, Rad-5®, Rad®-5v or SatShare® monitors.

Advanced blood parameter measurement systems are described in at least U.S. Pat. No. 7,647,083, filed Mar. 1, 2006, titled Multiple Wavelength Sensor Equalization; U.S. Pat. No. 7,729,733, filed Mar. 1, 2006, titled Configurable Physiological Measurement System; U.S. Pat. Pub. No. 2006/0211925, filed Mar. 1, 2006, titled Physiological Parameter Confidence Measure and U.S. Pat. Pub. No. 2006/0238358, filed Mar. 1, 2006, titled Noninvasive Multi-Parameter Patient Monitor, all assigned to Masimo Laboratories, Irvine, Calif. (Masimo Labs) and all incorporated by reference herein. An advanced parameter measurement system that includes acoustic monitoring is described in U.S. Pat. Pub. No. 2010/0274099, filed Dec. 21, 2009, titled Acoustic Sensor Assembly, assigned to Masimo and incorporated by reference herein.

Advanced blood parameter measurement systems include Masimo Rainbow® SET, which provides measurements in addition to $SpO_2$, such as total hemoglobin (SpHb™), oxygen content (SpOC™), methemoglobin (SpMet®), carboxyhemoglobin (SpCO®) and PVI®. Advanced blood parameter sensors include Masimo Rainbow® adhesive, ReSposable™ and reusable sensors. Advanced blood parameter monitors include Masimo Radical-7™, Rad-87™ and Rad-57™ monitors, all available from Masimo. Advanced parameter measurement systems may also include acoustic monitoring such as acoustic respiration rate (RRa™) using a Rainbow Acoustic Sensor™ and Rad-87™ monitor, available from Masimo. Such advanced pulse oximeters, low noise sensors and advanced physiological parameter measurement systems have also gained rapid acceptance in a wide variety of medical applications, including surgical wards, intensive care and neonatal units, general wards, home care, physical training, and virtually all types of monitoring scenarios.

FIGS. 1-3 illustrate problems and issues associated with physiological parameter measurement systems having fixed threshold alarm schemas. FIG. 1 illustrates a lower-limit, fixed-threshold alarm schema with respect to an oxygen saturation ($SpO_2$) parameter. Two alarm thresholds, $D_L$ (delay) and $ND_L$ (no delay), are defined. If oxygen saturation falls below $D_L$ for a time delay greater than TD, an alarm is triggered. If oxygen saturation falls below $ND_L$ an alarm is immediately triggered. $D_L$ 120 is typically set around or somewhat above 90% oxygen saturation and $ND_L$ 130 is typically set at 5% to 10% below $D_L$. For example, say a person's oxygen saturation 110 drops below $D_L$ 120 at $t=t_1$ 162 and stays below $D_L$ for at least a time delay TD 163. This triggers a delayed alarm 140 at $t=t_2$ 164, where $t_2=t_1+TD$. The alarm 140 remains active until oxygen saturation 110 rises above $D_L$ 120 at $t=t_3$ 166. As another example, say that oxygen saturation 110 then drops below $ND_L$ 130, which triggers an immediate alarm 150 at $t=t4$ 168. The alarm 150 remains active until oxygen saturation 110 rises above $D_L$ 120 at $t=t_5$ 169.

FIG. 2 illustrates an upper-limit, fixed-threshold alarm schema with respect to an oxygen saturation ($SpO_2$) parameter. This alarm scenario is particularly applicable to the avoidance of ROP (retinopathy of prematurity). Again, two alarm thresholds, $D_U$ (delay) and $ND_U$ (no delay), are defined. $D_U$ 220 might be set at or around 85% oxygen saturation and $ND_U$ 230 might be set at or around 90% oxygen saturation. For example, a neonate's oxygen saturation 210 rises above $D_U$ 220 at $t=t_1$ 262 and stays above $D_U$ for at least a time delay TD 263. This triggers a delayed alarm 240 at t=$t_2$ 264, where $t_2$=$t_1$+TD. The alarm 240 remains active until oxygen saturation 210 falls below $D_U$ 220 at t=$t_3$ 166. Oxygen saturation 210 then rises above $ND_U$ 230, which triggers an immediate alarm 250 at t=$t_4$ 268. The alarm 250 remains active until oxygen saturation 210 falls below $D_U$ 220 at t=$t_5$ 269.

FIG. 3 illustrates a baseline drift problem with the fixed threshold alarm schema described above. A person's oxygen saturation is plotted on an oxygen saturation (SpO$_2$) versus time graph 300. In particular, during a first time interval $T_1$ 362, a person has an oxygen saturation 310 with a relatively stable "baseline" 312 punctuated by a shallow, transient desaturation event 314. This scenario may occur after the person has been on oxygen so that baseline oxygen saturation is near 100%. Accordingly, with a fixed threshold alarm 330 set at, say, 90%, the transient event 314 does not trigger a nuisance alarm. However, the effects of oxygen treatments wear off over time and oxygen saturation levels drift downward 350. In particular, during a second time interval $T_2$ 364, a person has an oxygen saturation 320 with a relatively stable baseline 322. The later baseline 322 is established at a substantially lower oxygen saturation than the earlier baseline 312. In this scenario, a shallow, transient desaturation event 324 now exceeds the alarm threshold 330 and results in a nuisance alarm. After many such nuisance alarms, a caregiver may lower the alarm threshold 330 to unsafe levels or turn off alarms altogether, significantly hampering the effectiveness of monitoring oxygen saturation.

A fixed threshold alarm schema is described above with respect to an oxygen saturation parameter, such as derived from a pulse oximeter. However, problematic fixed threshold alarm behavior may be exhibited in a variety of parameter measurement systems that calculate physiological parameters related to circulatory, respiratory, neurological, gastrointestinal, urinary, immune, musculoskeletal, endocrine or reproductive systems, such as the circulatory and respiratory parameters cited above, as but a few examples.

An adaptive alarm system, as described in detail below, advantageously provides an adaptive threshold alarm to solve false alarm and missed true alarm problems associated with baseline drift among other issues. For example, for a lower limit embodiment, an adaptive alarm system adjusts an alarm threshold downwards when a parameter baseline is established at lower values. Likewise, for an upper limit embodiment, the adaptive alarm system adjusts an alarm threshold upwards in accordance with baseline drift so as to avoid nuisance alarms. In an embodiment, the rate of baseline movement is limited so as to avoid masking of transients. In an embodiment, the baseline is established along upper or lower portions of a parameter envelop so as to provide a margin of safety in lower limit or upper limit systems, respectively.

One aspect of an adaptive alarm system is responsive to a physiological parameter so as to generate an alarm threshold that adapts to baseline drift in the parameter and reduce false alarms without a corresponding increase in missed true alarms. The adaptive alarm system has a parameter derived from a physiological measurement system using a sensor in communication with a living being. A baseline processor calculates a parameter baseline from an average value of the parameter. Parameter limits specify an allowable range of the parameter. An adaptive threshold processor calculates an adaptive threshold from the parameter baseline and the parameter limits. An alarm generator is responsive to the parameter and the adaptive threshold so as to trigger an alarm indicative of the parameter crossing the adaptive threshold. The adaptive threshold is responsive to the parameter baseline so as to increase in value as the parameter baseline drifts to a higher parameter value and to decrease in value as the parameter baseline drifts to a lower parameter value.

In various embodiments, the baseline processor has a sliding window that identifies a time slice of parameter values. A trend calculator determines a trend from an average of the parameter values in the time slice. A response limiter tracks only the relatively long-term transitions of the trend. A bias calculator deletes the highest parameter values in the time slice or the lowest parameter values in the time slice so as to adjust the baseline to either a lower value or a higher value, respectively. The adaptive threshold becomes less response to baseline drift as the baseline approaches a predefined parameter limit. A first adaptive threshold is responsive to lower parameter limits and a second adaptive threshold is responsive to upper parameter limits. The alarm generator is responsive to both positive and negative transients from the baseline according to the first adaptive threshold and the second adaptive threshold. The first adaptive threshold is increasingly responsive to negative transients and the second adaptive threshold is decreasingly responsive to positive transients as the baseline trends toward lower parameter values.

Another aspect of an adaptive alarm system measures a physiological parameter, establishes a baseline for the parameter, adjusts an alarm threshold according to drift of the baseline and triggers an alarm in response to the parameter measurement crossing the alarm threshold. In various embodiments, the baseline is established by biasing a segment of the parameter, calculating a biased trend from the biased segment and restricting the transient response of the biased trend. The alarm threshold is adjusted by setting a parameter limit and calculating a delta difference between the alarm threshold and the baseline as a linear function of the baseline according to the parameter limit. The delta difference is calculated by decreasing delta as the baseline drifts toward the parameter limit and increasing delta as the baseline drifts away from the parameter limit. A parameter limit is set by selecting a first parameter limit in relation to a delayed alarm and selecting a second parameter limit in relation to an un-delayed alarm. A segment of the parameter is biased by windowing the parameter measurements, removing a lower value portion of the windowed parameter measurements and averaging a remaining portion of the windowed parameter measurements. An upper delta difference between an upper alarm threshold and the baseline is calculated and a lower delta difference between a lower alarm threshold and the baseline is calculated.

A further aspect of an adaptive alarm system has a baseline processor that inputs a parameter and outputs a baseline according to a trend of the parameter. An adaptive threshold processor establishes an alarm threshold at a delta difference from the baseline. An alarm generator triggers an alarm based upon a parameter transient from the baseline crossing the alarm threshold. In various embodiments, a trend calculator outputs a biased trend and the baseline is responsive to the biased trend so as to reduce the size of a transient that triggers the alarm. A response limiter reduces baseline movement due to parameter transients. The adaptive threshold processor establishes a lower alarm threshold below the baseline and an upper alarm threshold above the baseline so that the alarm generator is responsive to both positive and negative transients from the baseline. The baseline processor establishes a lower baseline biased above the parameter trend and an upper baseline biased below the parameter trend. The lower alarm threshold is increasingly responsive to negative transients and the upper alarm threshold is decreasingly responsive to positive transients as the baseline trends toward lower parameter values.

DESCRIPTION OF THE DRAWINGS

FIGS. 4A-B are general block diagrams of an adaptive alarm system having lower parameter limits;

FIGS. 5A-B are a graph of a physiological parameter versus delta space and a graph of delta versus baseline, respectively, illustrating the relationship between a baseline, a lower-limit adaptive threshold and a variable difference delta between the baseline and the adaptive threshold;

FIGS. 9A-B are general block diagrams of an adaptive alarm system having upper parameter limits;

DETAILED DESCRIPTION OF THE PREFERRED EMBODIMENTS

Figure 1:
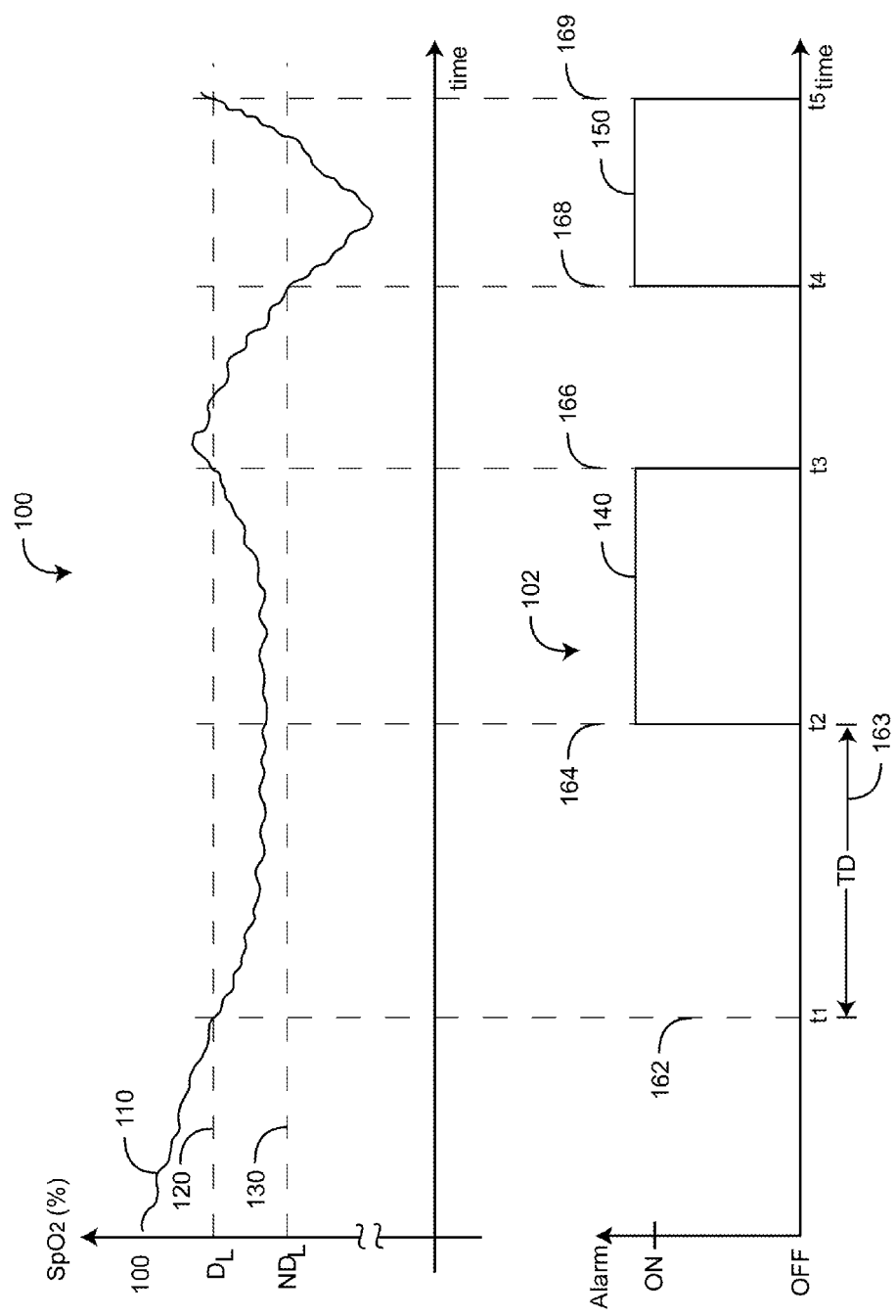
FIGS. 1-3 are exemplar graphs illustrating problems and issues associated with physiological parameter measurement systems having fixed threshold alarm schemas.
Figure 2:
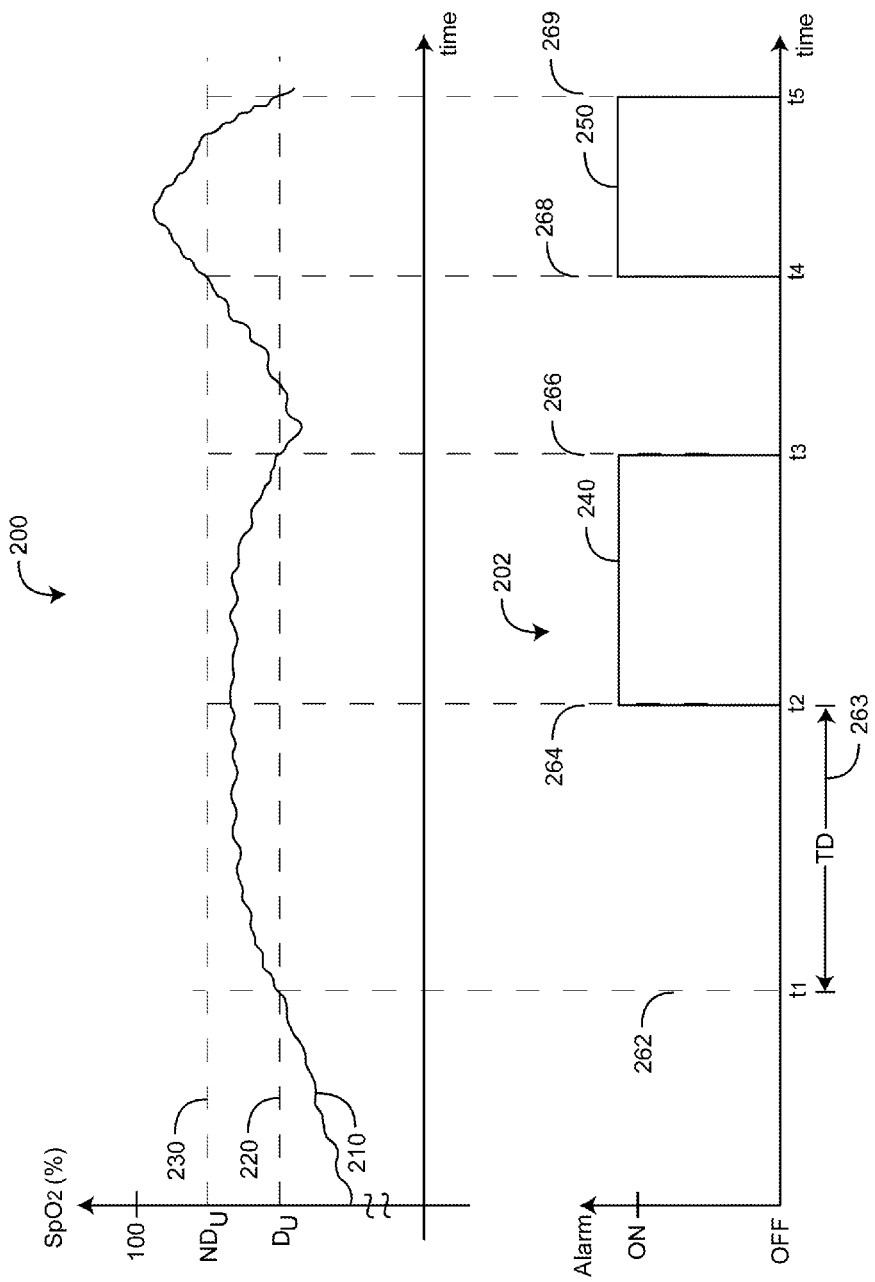
Figure 3:
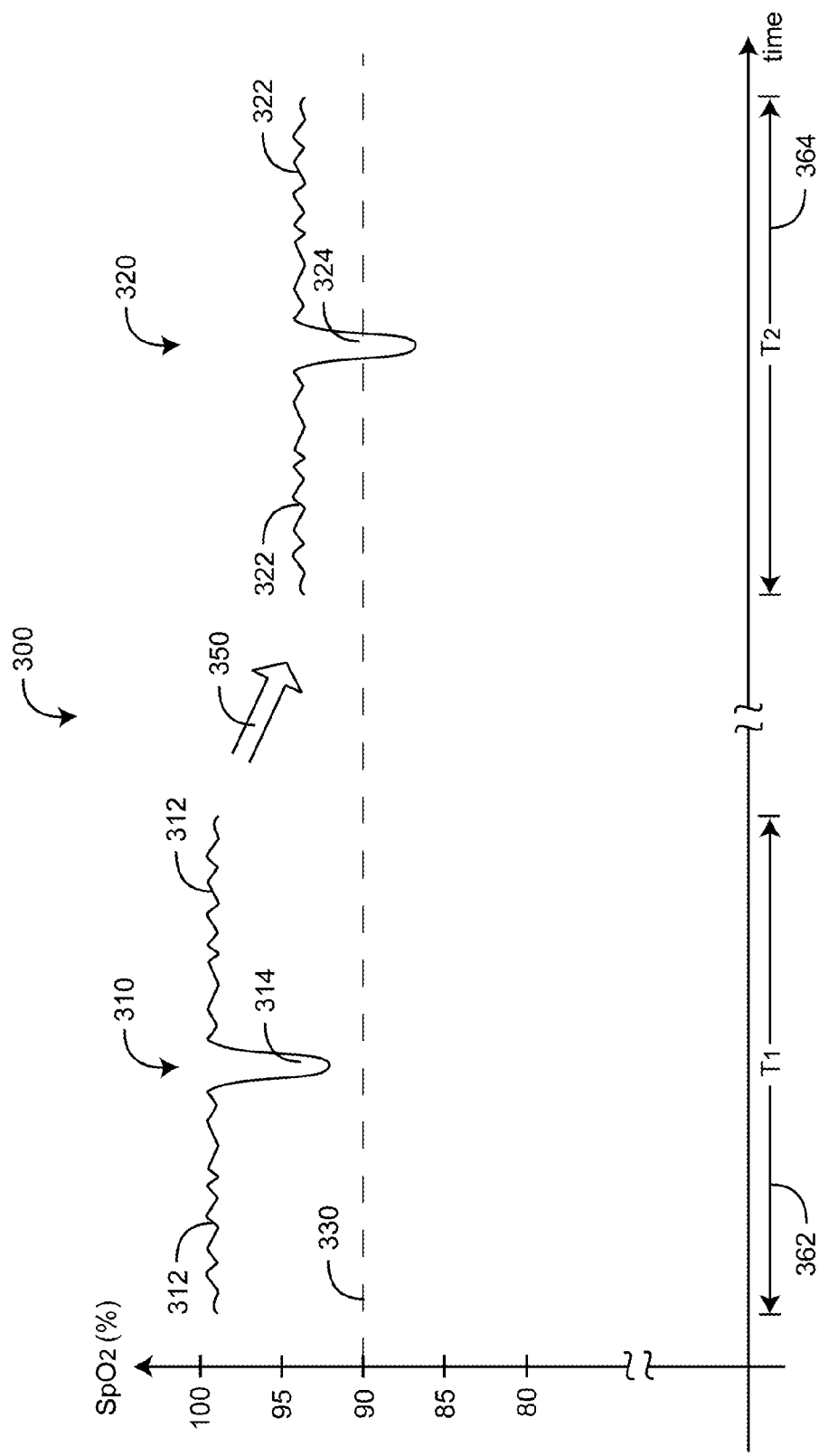

FIGS. 4A-B illustrate an adaptive alarm system 400 embodiment having lower parameter limits $L_1$ and $L_2$. As shown in FIG. 4A, the adaptive alarm system 400 has parameter 401, first limit ($L_1$) 403, second limit ($L_2$) 405 and maximum parameter value (Max) 406 inputs and generates a corresponding alarm 412 output. The parameter 401 input is generated by a physiological parameter processor, such as a pulse oximeter or an advanced blood parameter processor described above, as examples. The adaptive alarm system 400 has an alarm generator 410, a baseline processor 420, and an adaptive threshold processor 440. The alarm generator 410 has parameter 401 and adaptive threshold (AT) 442 inputs and generates the alarm 412 output accordingly. A baseline processor 420 has the parameter 401 input and generates a parameter baseline (B) 422 output. The baseline processor 420, is described in detail with respect to FIG. 4B, below. An adaptive threshold processor 440 has parameter baseline (B) 422, $L_1$ 403, $L_2$ 405 and Max 406 inputs and generates the adaptive threshold (AT) 442. The adaptive threshold processor 440 is described in detail with respect to FIGS. 5A-B, below.

As shown in FIG. 4A, in an embodiment $L_1$ 403 and $L_2$ 405 may correspond to conventional fixed alarm thresholds with and without an alarm time delay, respectively. For an adaptive threshold schema, however, $L_1$ 403 and $L_2$ 405 do not determine an alarm threshold per se, but are reference levels for determining an adaptive threshold (AT) 442. In an embodiment, $L_1$ 403 is an upper limit of the adaptive alarm threshold AT when the baseline is near the maximum parameter value (Max), and $L_2$ 405 is a lower limit of the adaptive alarm threshold, as described in detail with respect to FIGS. 5A-B, below. In an exemplar embodiment when the parameter is oxygen saturation, $L_1$ 403 is set at or around 90% and $L_2$ 405 is set at 5 to 10% below $L_1$, i.e. at 85% to 80% oxygen saturation. Many other $L_1$ and $L_2$ values may be used for an adaptive threshold schema as described herein.

Also shown in FIG. 4A, in an embodiment the alarm 412 output is triggered when the parameter 401 input falls below AT 442 and ends when the parameter 401 input rises above AT 442 or is otherwise cancelled. In an embodiment, the alarm 412 output is triggered after a time delay (TD), which may be fixed or variable. In an embodiment, the time delay (TD) is a function of the adaptive threshold (AT) 442. In an embodiment, the time delay (TD) is zero when the adaptive threshold (AT) is at the second lower limit ($L_2$) 405.

As shown in FIG. 4B, a baseline processor 420 embodiment has a sliding window 450, a bias calculator 460, a trend calculator 470 and a response limiter 480. The sliding window 450 inputs the parameter 401 and outputs a time segment 452 of the parameter 401. In an embodiment, each window incorporates a five minute span of parameter values. The bias calculator 460 advantageously provides an upward shift in the baseline (B) 422 for an additional margin of error over missed true alarms. That is, a baseline 422 is generated that tracks a higher-than-average range of parameter values, effectively raising the adaptive threshold AT slightly above a threshold calculated based upon a true parameter average, as shown and described in detail with respect to FIGS. 7-8, below. In an embodiment, the bias calculator 460 rejects a lower range of parameter values from each time segment 452 from the sliding window so as to generate a biased time segment 462.

Also shown in FIG. 4B, the trend calculator 470 outputs a biased trend 472 of the remaining higher range of parameter values in each biased segment 462. In an embodiment, the biased trend 462 is an average of the values in the biased time segment 462. In other embodiments, the biased trend 462 is a median or mode of the values in the biased time segment 462. The response limiter 480 advantageously limits the extent to which the baseline 422 output tracks the biased trend 472. Accordingly, the baseline 422 tracks only relatively longer-lived transitions of the parameter, but does not track (and hence mask) physiologically significant parameter events, such as oxygen desaturations for a $SpO_2$ parameter to name but one example. In an embodiment, the response limiter 480 has a low pass transfer function. In an embodiment, the response limiter 480 is a slew rate limiter.

FIGS. 5A-B further illustrate an adaptive threshold processor 440 (FIG. 4A) having a baseline (B) 422 input and generating an adaptive threshold (AT) 442 output and a delta (Δ) 444 ancillary output according to parameter limits $L_1$ 403, $L_2$ 405 and Max 406, as described above. As shown in FIG. 5A, as the baseline (B) 422 decreases (increases) the adaptive threshold (AT) 444 monotonically decreases (increases) between $L_1$ 403 and $L_2$ 405. Further, as the baseline (B) 422 decreases (increases) the delta (Δ) 444 difference between the baseline (B) 422 and the adaptive threshold (AT) 442 monotonically decreases (increases) between Max–$L_1$ and zero.

As shown in FIG. 5B, the relationship between the delta (Δ) 444 and the baseline (B) 444 may be linear 550 (solid line), non-linear 560 (small-dash lines) or piecewise-linear (large-dash lines), to name a few. In an embodiment, the adaptive threshold processor 440 (FIG. 4A) calculates an adaptive threshold (AT) 442 output in response to the baseline (B) 422 input according to a linear relationship. In a linear embodiment, the adaptive threshold processor 440 (FIG. 4A) calculates the adaptive threshold (AT) 442 according to EQS. 1-2:

$$\Delta = -\left(\frac{\text{Max} - L_1}{\text{Max} - L_2}\right)(\text{Max} - B) + (\text{Max} - L_1) \quad (1)$$

$$AT = B - \Delta \quad (2)$$

where Δ=Max–$L_1$ @ B=Max; Δ=0 @ B=$L_2$
and where AT=$L_1$ @ B=Max; AT=$L_2$ @ B=$L_2$, accordingly.

Figure 6:
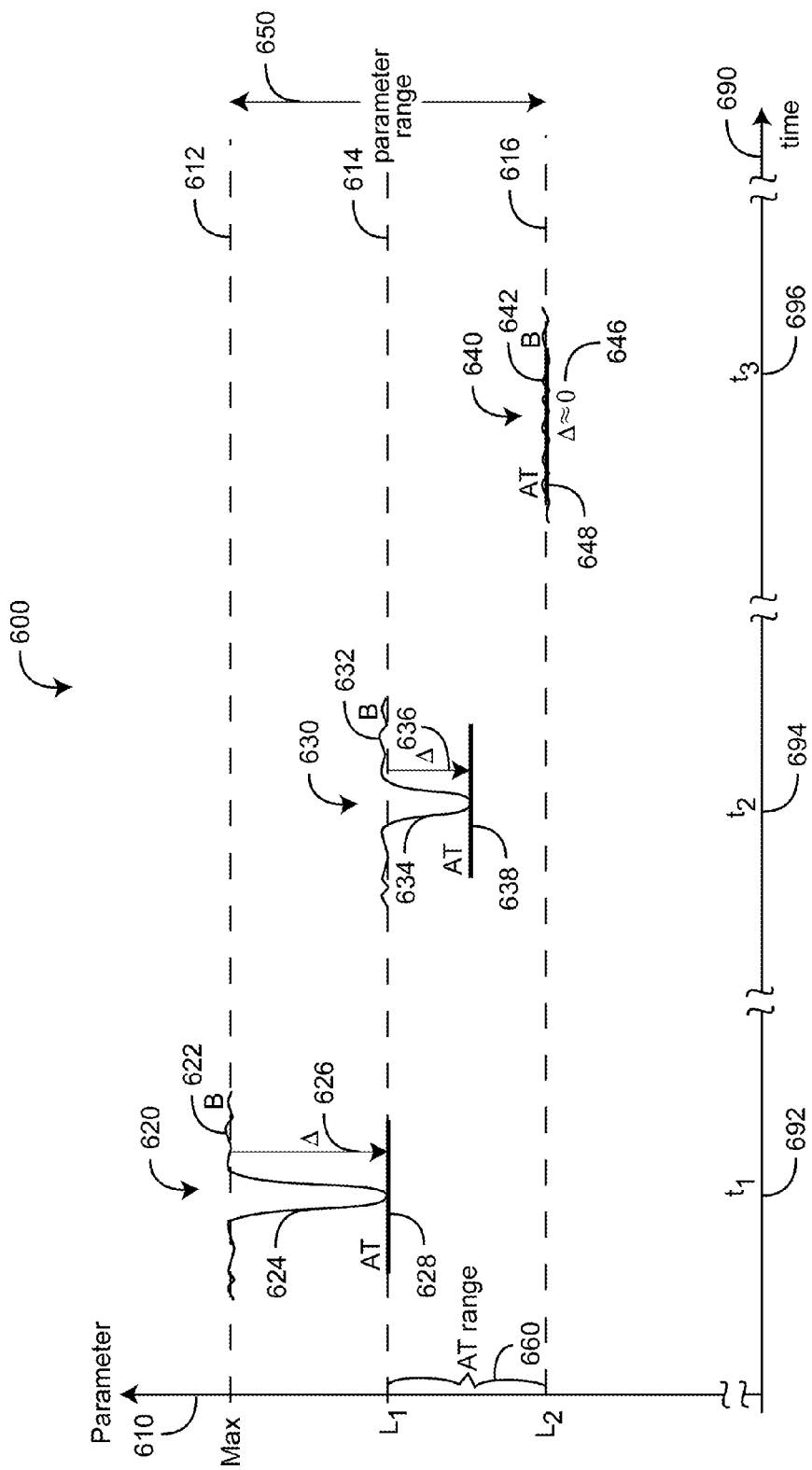
FIG. 6 is an exemplar graph of a physiological parameter versus time illustrating an adaptive alarm system having a lower-limit adaptive threshold.

FIG. 6 illustrates the operational characteristics an adaptive alarm system 400 (FIG. 4A) having parameter limits Max 612, $L_1$ 614 and $L_2$ 616 and an alarm responsive to a baseline (B) 622, 632, 642; an adaptive threshold (AT) 628, 638, 648; and a corresponding Δ 626, 636, 646 according to EQS. 1-2, above. In particular, a physiological parameter 610 is graphed versus time 690 for various time segments $t_1$, $t_2$, $t_3$ 692-696. The parameter range (PR) 650 is:

$$PR = \text{Max} - L_2 \quad (3)$$

and the adaptive threshold range (ATR) 660 is:

$$ATR = L_1 - L_2 \quad (4)$$

As shown in FIG. 6, during a first time period $t_1$ 692, a parameter segment 620 has a baseline (B) 622 at about Max 612. As such, Δ 626=Max–$L_1$ and the adaptive threshold (AT) 628 is at about $L_1$ 614. Accordingly, a transient 624 having a size less than Δ 626 does not trigger the alarm 412 (FIG. 4A).

Also shown in FIG. 6, during a second time period $t_2$ 694, a parameter segment 630 has a baseline (B) 632 at about $L_1$ 614. As such, Δ 636 is less than Max–$L_1$ and the adaptive threshold (AT) 638 is between $L_1$ and $L_2$. Accordingly, a smaller transient 634 will trigger the alarm as compared to a transient 624 in the first time segment.

Further shown in FIG. 6, during a third time period $t_3$ 696, a parameter segment 640 has a baseline (B) 642 at about $L_2$ 616. As such, Δ 646 is about zero and the adaptive threshold (AT) 648 is at about $L_2$. Accordingly, even a small negative transient will trigger the alarm. As such, the behavior of the alarm threshold AT 628, 638, 648 advantageously adapts to higher or lower baseline values so as to increase or decrease the size of negative transients that trigger or do not trigger the alarm 412 (FIG. 4A).

Figure 7:
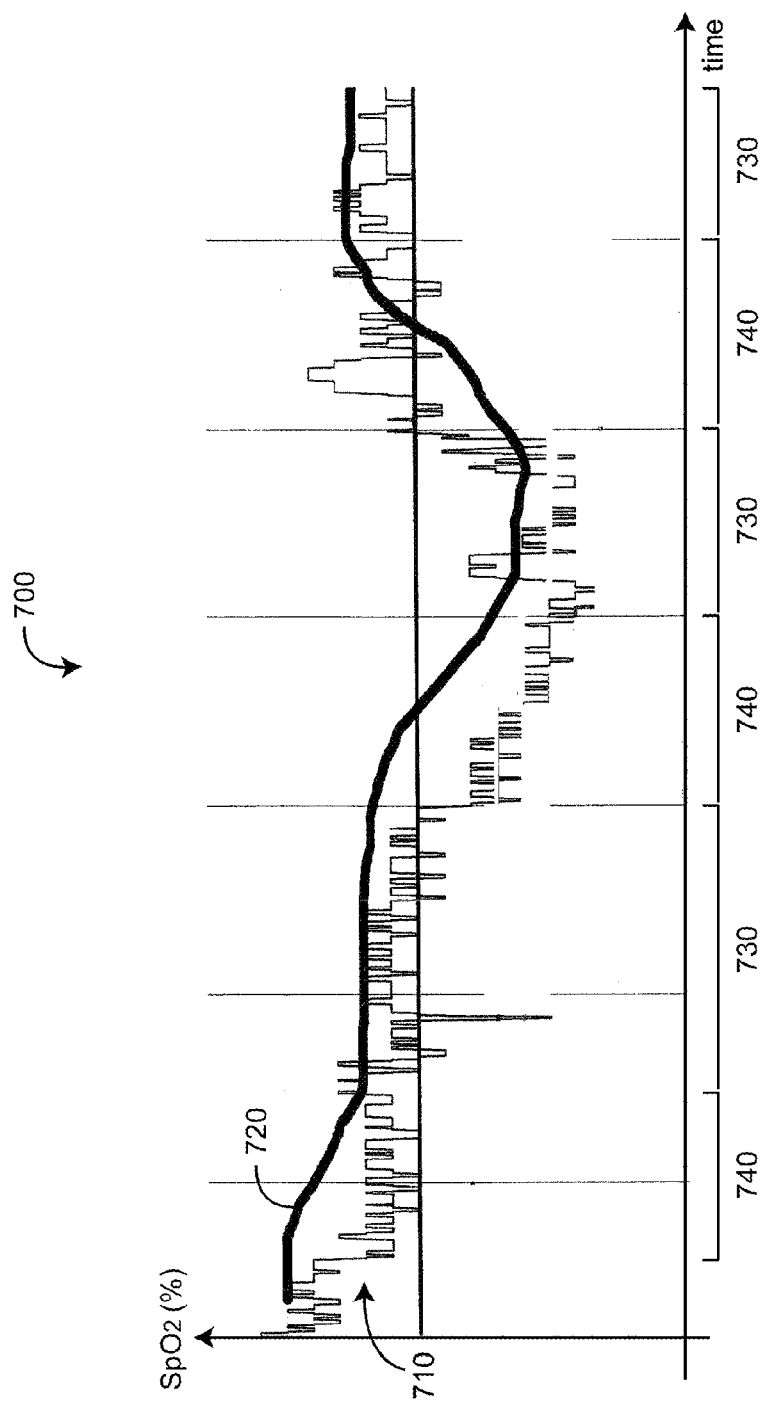
FIG. 7 is a graph of oxygen saturation versus time illustrating a baseline for determining an adaptive threshold.

FIG. 7 is a parameter versus time graph 700 illustrating the characteristics of an adaptive alarm system 400 (FIGS. 4A-B), as described with respect to FIGS. 4-6, above, where the parameter is oxygen saturation ($SpO_2$). The graph 700 has a $SpO_2$ trace 710 and a superimposed baseline trace 720. The graph 700 also delineates tracking periods 730, where the baseline 720 follows the upper portions of $SpO_2$ values, and lagging periods 740, where the baseline 720 does not follow transient $SpO_2$ events. The tracking time periods 730 illustrate that the baseline 720 advantageously tracks at the higher range of $SpO_2$ values 710 during relatively stable (flat) periods, as described above. Lagging time periods 740 illustrate that the baseline 720 is advantageously limited in response to transient desaturation events so that significant desaturations fall below an adaptive threshold (not shown) and trigger an alarm accordingly.

Figure 8:
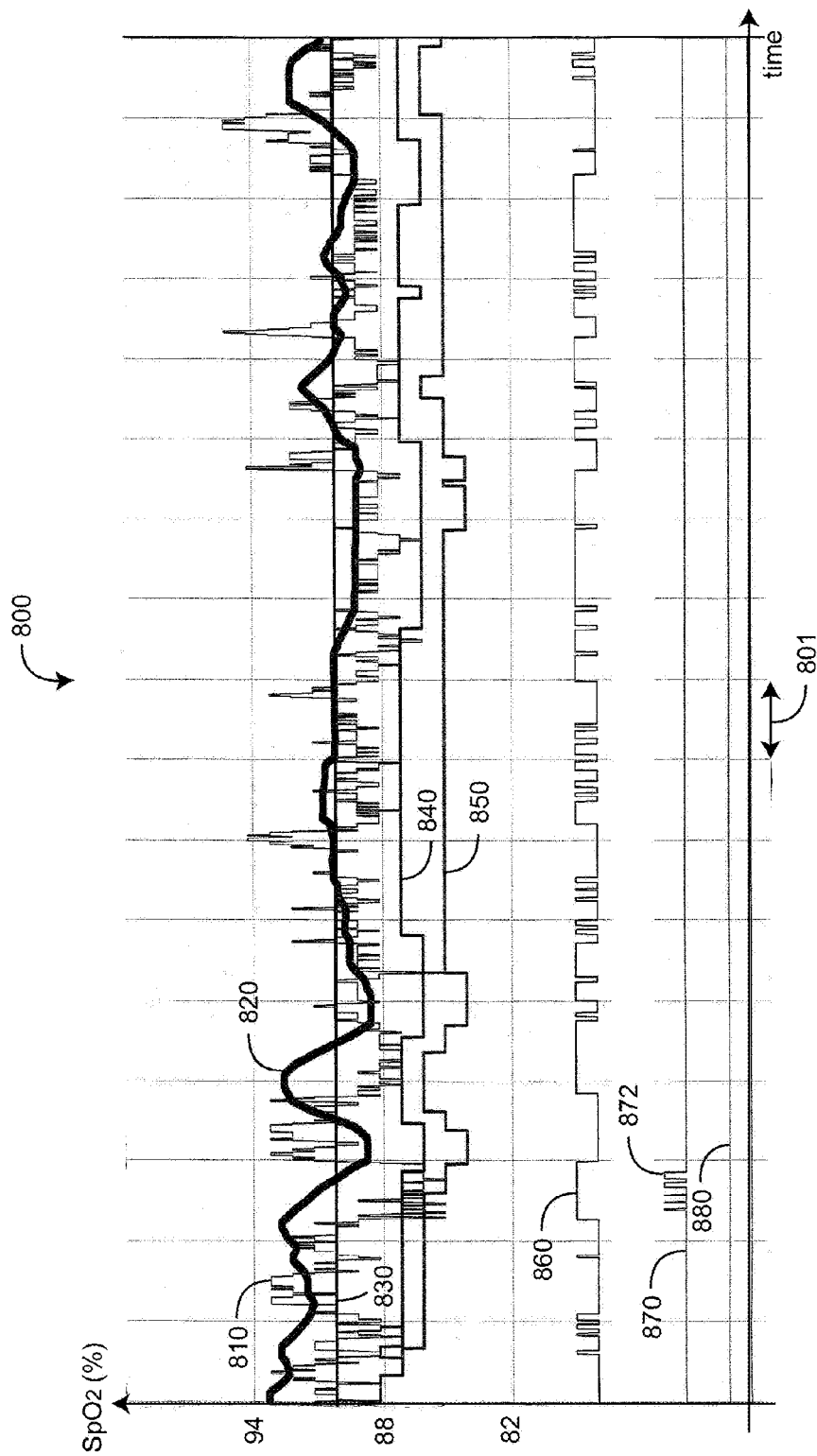
FIG. 8 is a graph of oxygen saturation versus time comparing adaptive-threshold alarm performance with fixed-threshold alarm performance.

FIG. 8 is a parameter versus time graph 800 illustrating characteristics of an adaptive alarm system 400 (FIGS. 4A-B), as described with respect to FIGS. 4-6, above, where the parameter is oxygen saturation ($SpO_2$). Vertical axis ($SpO_2$) resolution is 1%. The time interval 801 between vertical hash marks is five minutes. The graph 800 has a $SpO_2$ trace 810 and a baseline trace 820. The graph 800 also has a fixed threshold trace 830, a first adaptive threshold (AT) trace 840 and a second AT trace 850. The graph 800 further has a fixed threshold alarm trace 860, a first adaptive threshold alarm trace 870 and a second adaptive threshold alarm trace 880. In this example, $L_1$ is 90% and $L_2$ is 85% for the first AT trace 840 and first AT alarm trace 870. $L_2$ is 80% for a second AT trace 850 and a second AT alarm trace 880. The fixed threshold 830 results in many nuisance alarms 860. By comparison, the adaptive threshold alarm with $L_2$=85% has just one time interval of alarms 872 during a roughly 6% desaturation period (from 92% to 86%). The adaptive threshold alarm with $L_2$=80%, has no alarms during the 1 hour 25 minute monitoring period.

FIGS. 9A-B illustrate an adaptive alarm system 900 embodiment having upper parameter limits $U_1$ and $U_2$. As shown in FIG. 9A, the adaptive alarm system 900 has parameter 901, first limit ($U_1$) 903, second limit ($U_2$) 905 and minimum parameter value (Min) 906 inputs and generates a corresponding alarm 912 output. The parameter 901 input is generated by a physiological parameter processor, such as a pulse oximeter or an advanced blood parameter processor described above, as examples. The adaptive alarm system 900 has an alarm generator 910, a baseline processor 920, and an adaptive threshold processor 940. The alarm generator 910 has parameter 901 and adaptive threshold (AT) 942 inputs and generates the alarm 912 output accordingly. A baseline processor 920 has the parameter 901 input and generates a parameter baseline (B) 922 output. The baseline processor 920, is described in detail with respect to FIG. 9B, below. An adaptive threshold processor 940 has parameter baseline (B) 922, $U_1$ 903, $U_2$ 905 and Min 906 inputs and generates the adaptive threshold (AT) 942. The adaptive threshold processor 940 is described in detail with respect to FIGS. 10A-B, below.

As shown in FIG. 9A, in an embodiment $U_1$ 903 and $U_2$ 905 may correspond to conventional fixed alarm thresholds with and without an alarm time delay, respectively. For an adaptive threshold schema, however, $U_1$ 903 and $U_2$ 905 do not determine an alarm threshold per se, but are reference levels for determining an adaptive threshold (AT) 942. In an embodiment, $U_1$ 903 is a lower limit of the adaptive alarm threshold AT when the baseline is near the minimum parameter value (Min), and $U_2$ 905 is an upper limit of the adaptive alarm threshold, as described in detail with respect to FIGS. 10A-B, below. In an exemplar embodiment when the parameter is oxygen saturation, $U_1$ 903 is set at or around 85% and $U_2$ 905 is set at or around 90% oxygen saturation. Many other $U_1$ and $U_2$ values may be used for an adaptive threshold schema as described herein.

Also shown in FIG. 9A, in an embodiment the alarm 912 output is triggered when the parameter 901 input rises above AT 942 and ends when the parameter 901 input falls below AT 942 or is otherwise cancelled. In an embodiment, the alarm 912 output is triggered after a time delay (TD), which may be fixed or variable. In an embodiment, the time delay (TD) is a function of the adaptive threshold (AT) 942. In an embodiment, the time delay (TD) is zero when the adaptive threshold (AT) is at the second upper limit ($U_2$) 905.

As shown in FIG. 9B, a baseline processor 920 embodiment has a sliding window 950, a bias calculator 960, a trend calculator 970 and a response limiter 980. The sliding window 950 inputs the parameter 901 and outputs a time segment 952 of the parameter 901. In an embodiment, each window incorporates a five minute span of parameter values. The bias calculator 960 advantageously provides a downward shift in the baseline (B) 922 for an additional margin of error over missed true alarms. That is, a baseline 922 is generated that tracks a lower-than-average range of parameter values, effectively lowering the adaptive threshold AT slightly below a threshold calculated based upon a true parameter average. In an embodiment, the bias calculator 960 rejects an upper range of parameter values from each time segment 952 from the sliding window so as to generate a biased time segment 962.

Also shown in FIG. 9B, the trend calculator 970 outputs a biased trend 972 of the remaining lower range of parameter values in each biased segment 962. In an embodiment, the biased trend 962 is an average of the values in the biased time segment 962. In other embodiments, the biased trend 962 is a median or mode of the values in the biased time segment 962. The response limiter 980 advantageously limits the extent to which the baseline 922 output tracks the biased trend 972. Accordingly, the baseline 922 tracks only relatively longer-lived transitions of the parameter, but does not track (and hence mask) physiologically significant parameter events, such as oxygen desaturations for a $SpO_2$ parameter to name but one example. In an embodiment, the response limiter 980 has a low pass transfer function. In an embodiment, the response limiter 980 is a slew rate limiter.

Figure 10B:
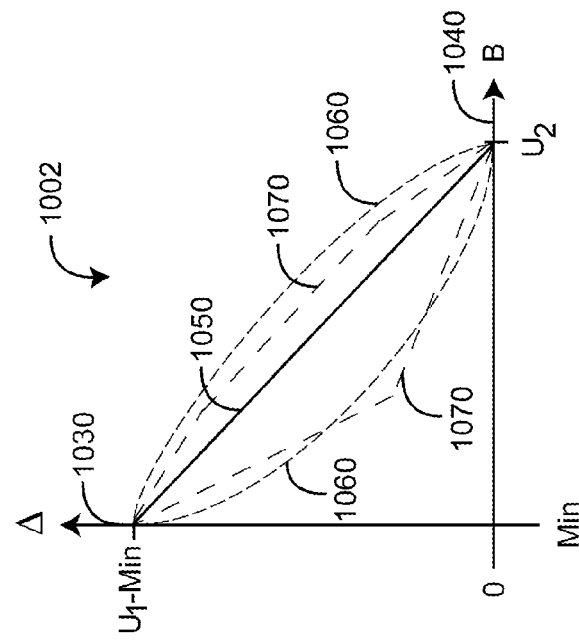
FIGS. 10A-B are a graph of a physiological parameter versus delta space and a graph of delta versus baseline, respectively, illustrating the relationship between a baseline, an upper-limit adaptive threshold and a variable delta difference between the baseline and the adaptive threshold.
Figure 10A:
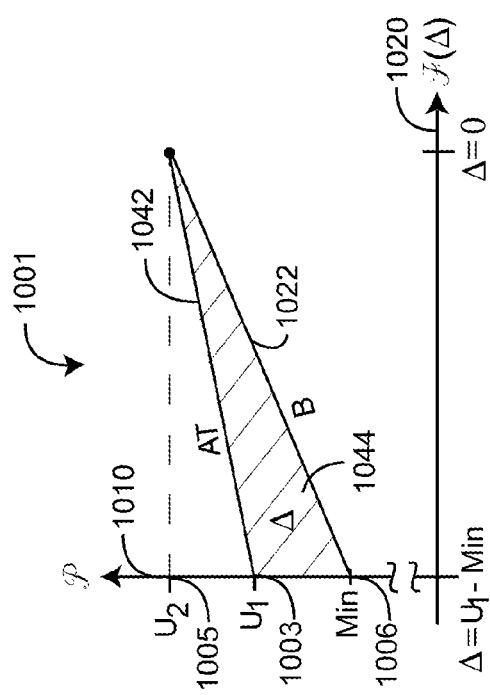

FIGS. 10A-B further illustrate an adaptive threshold processor 940 (FIG. 9A) having a baseline (B) 922 input and generating an adaptive threshold (AT) 942 output and a delta (Δ) 944 ancillary output according to parameter limits $U_1$ 903, $U_2$ 905 and Min 906, as described above. As shown in FIG. 10A, as the baseline (B) 922 decreases (increases) the adaptive threshold (AT) 944 monotonically decreases (increases) between $U_1$ 903 and $U_2$ 905. Further, as the baseline (B) 922 decreases (increases) the delta (Δ) 944 difference between the baseline (B) 922 and the adaptive threshold (AT) 942 monotonically decreases (increases) between Min–$U_1$ and zero.

As shown in FIG. 10B, the relationship between the delta (Δ) 944 and the baseline (B) 944 may be linear 550 (solid line), non-linear 560 (small-dash lines) or piecewise-linear (large-dash lines), to name a few. In an embodiment, the adaptive threshold processor 940 (FIG. 9A) calculates an adaptive threshold (AT) 942 output in response to the baseline (B) 922 input according to a linear relationship. In a linear embodiment, the adaptive threshold processor 940 (FIG. 9A) calculates the adaptive threshold (AT) 942 according to EQS. 5-6:

$$\Delta = -\left(\frac{U_1 - \text{Min}}{U_2 - \text{Min}}\right)(B - \text{Min}) + (U_1 - \text{Min}) \quad (5)$$

$$AT = B + \Delta \quad (6)$$

where Δ=$U_1$–Min @ B=Min; Δ=0 @ B=$U_2$
and where AT=$U_1$ @ B=Min; AT=$U_2$ @ B=$U_2$, accordingly.

Figure 11:
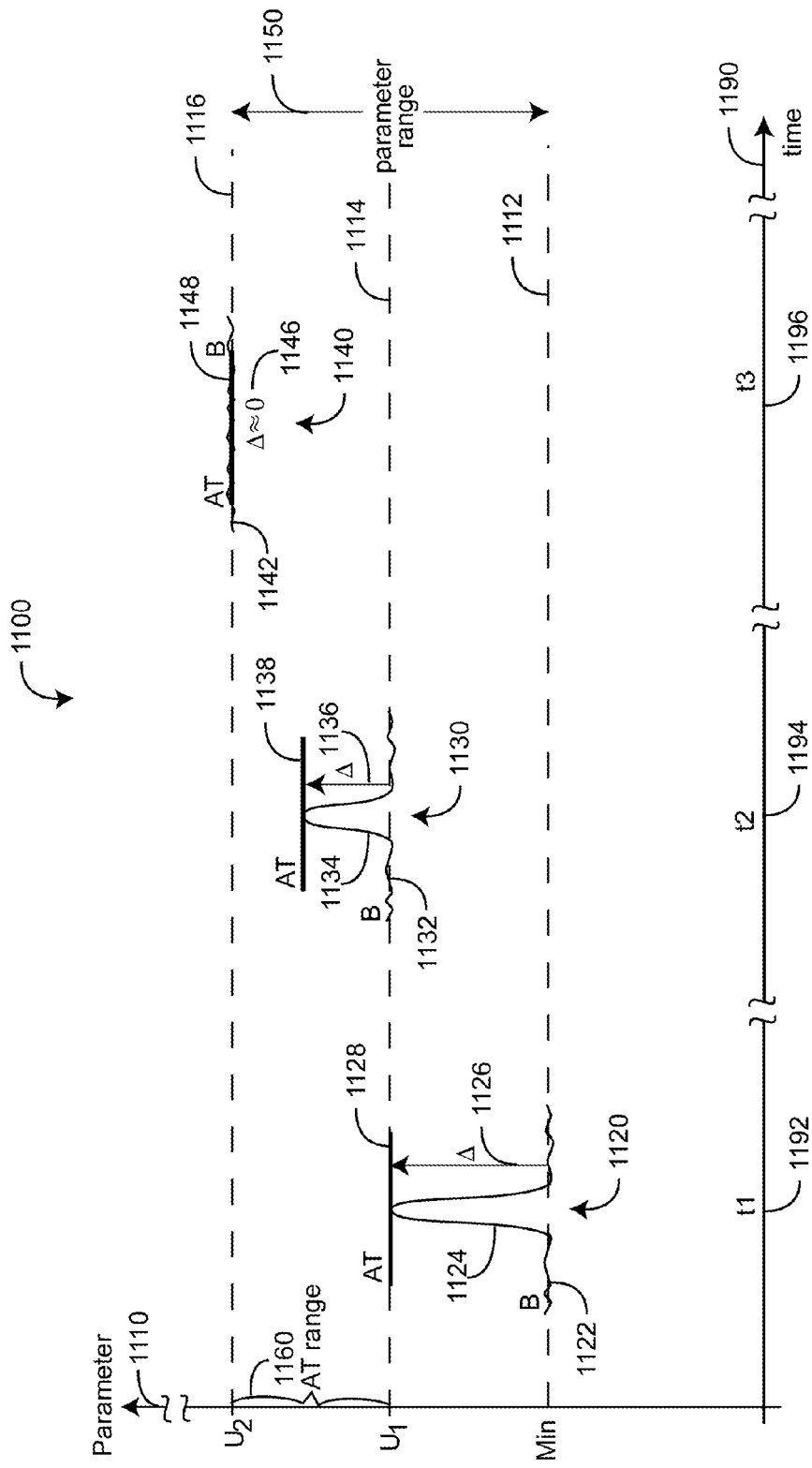
FIG. 11 is an exemplar graph of a physiological parameter versus time illustrating an adaptive alarm system having an upper-limit adaptive threshold.

FIG. 11 illustrates the operational characteristics an adaptive alarm system 900 (FIG. 9A) having parameter limits Min 1112, $U_1$ 1114 and $U_2$ 1116 and an alarm responsive to a baseline (B) 1122, 1132, 1142; an adaptive threshold (AT) 1128, 1138, 1148; and a corresponding Δ 1126, 1136, 1146 according to EQS. 5-6, above. In particular, a physiological parameter 1110 is graphed versus time 1190 for various time segments $t_1$, $t_2$, $t_3$ 1192-1196. The parameter range (PR) 1150 is:

$$PR = U_2 - \text{Min} \quad (7)$$

and the adaptive threshold range (ATR) 1160 is:

$$ATR = U_2 - U_1 \quad (8)$$

As shown in FIG. 11, during a first time period $t_1$ 1192, a parameter segment 1120 has a baseline (B) 1122 at about Min 1112. As such, Δ 1126=$U_1$–Min and the adaptive threshold (AT) 1128 is at about $U_1$ 1114. Accordingly, a transient 1124 having a size less than Δ 1126 does not trigger the alarm 912 (FIG. 9A).

Also shown in FIG. 11, during a second time period $t_2$ 1194, a parameter segment 1130 has a baseline (B) 1132 at about $U_1$ 1114. As such, Δ 1136 is less than $U_1$–Min and the adaptive threshold (AT) 1138 is between $U_1$ and $U_2$. Accordingly, a smaller transient 1134 will trigger the alarm as compared to a transient 1124 in the first time segment.

Further shown in FIG. 11, during a third time period $t_3$ 1196, a parameter segment 1140 has a baseline (B) 1142 at about $U_2$ 1116. As such, Δ 1146 is about zero and the adaptive threshold (AT) 1148 is at about $U_2$. Accordingly, even a small positive transient will trigger the alarm. As such, the behavior of the alarm threshold AT 1128, 1138, 1148 advantageously adapts to higher or lower baseline values so as to increase or decrease the size of positive transients that trigger or do not trigger the alarm 912 (FIG. 9A).

Figure 12A:
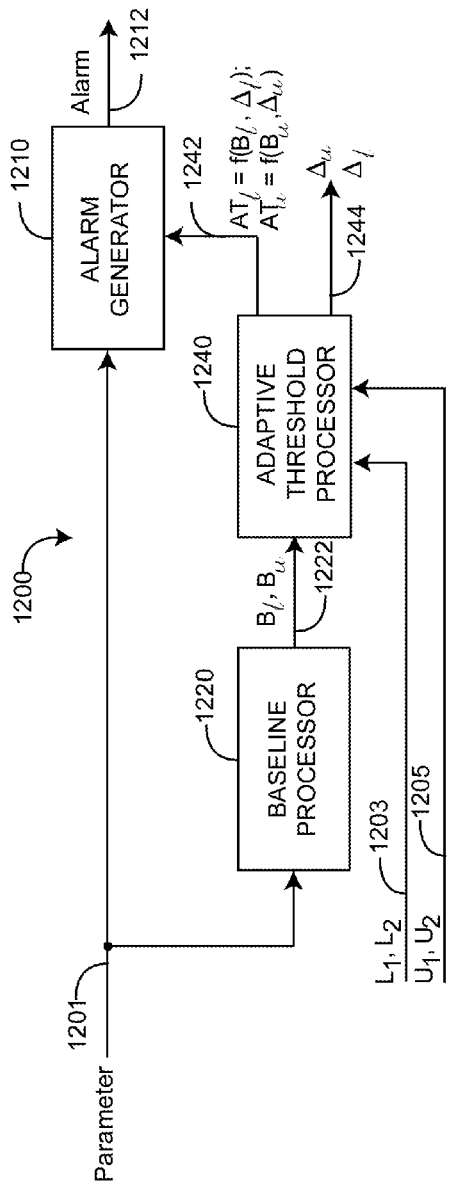
FIGS. 12A-B are general block diagrams of an adaptive alarm system having both lower alarm limits and upper alarm limits.
Figure 12B:
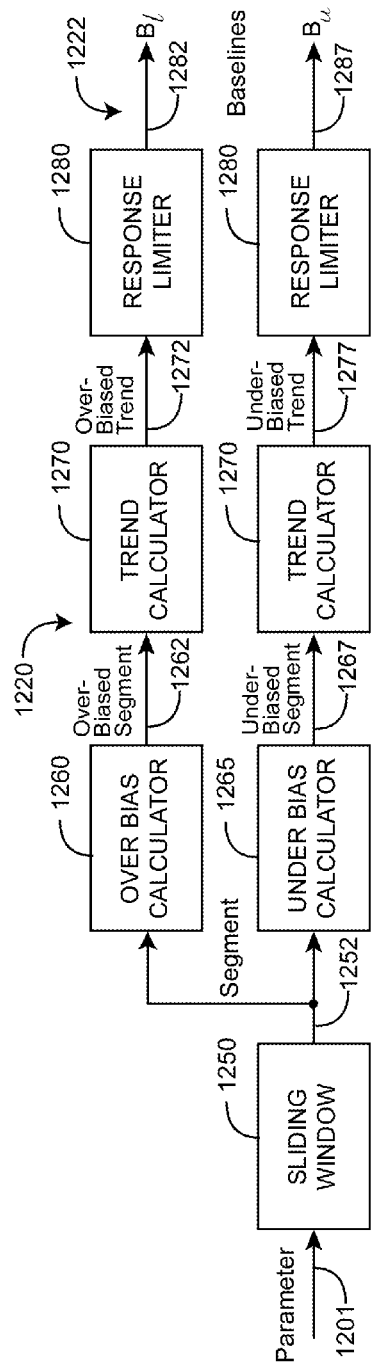

FIGS. 12A-B illustrate an adaptive alarm system 1200 embodiment having lower limits $L_1$, $L_2$ 1203, such as described with respect to FIGS. 4A-B above, or upper limits $U_1$, $U_2$ 1205 such as described with respect to FIGS. 9A-B above, or both. As shown in FIG. 12A, the adaptive alarm system 1200 has parameter 1201, lower limit 1203 and upper limit 1205 inputs and generates a corresponding alarm 1212 output. The parameter 1201 input is generated by a physiological parameter processor, such as a pulse oximeter or an advanced blood parameter processor described above, as examples. The adaptive alarm system 1200 has an alarm generator 1210, a baseline processor 1220 and an adaptive threshold processor 1240. The alarm generator 1210 has parameter 1201 and adaptive threshold (AT) 1242 inputs and generates the alarm 1212 output accordingly. A baseline processor 1220 has the parameter 1201 input and generates one or more parameter baseline 1222 outputs. The baseline processor 1220, is described in detail with respect to FIG. 12B, below. An adaptive threshold processor 1240 has parameter baseline 1222, lower limit $L_1$, $L_2$ 1203 and upper limit $U_1$, $U_2$ 1205 inputs and generates lower and upper adaptive threshold $AT_l$, $AT_u$ 1242 outputs. The adaptive threshold processor 1240 also generates ancillary upper and lower delta 1244 outputs. The adaptive threshold processor 1240 is described in detail with respect to FIGS. 13A-E, below.

As shown in FIG. 12A, in an embodiment $L_1$, $L_2$ 1203 and $U_1$, $U_2$ 1205 may correspond to conventional fixed alarm thresholds with an alarm delay ($L_1$, $U_1$) and without an alarm delay ($L_2$, $U_2$). For an adaptive threshold schema, however, these limits 1203, 1205 do not determine an alarm threshold per se, but are reference levels for determining lower and upper adaptive thresholds $AT_l$, $AT_u$ 1242.

Also shown in FIG. 12A, in an embodiment the alarm 1212 output is triggered when the parameter 1201 input falls below $AT_l$ 1242 and ends when the parameter 1201 input rises above $AT_l$ 1242 or the alarm is otherwise cancelled. Further, the alarm 1212 output is triggered when the parameter 1201 input rises above $AT_u$ 1242 and ends when the parameter 1201 input falls below $AT_u$ 1242 or the alarm is otherwise cancelled. In an embodiment, the alarm 1212 output is triggered after a time delay (TD), which may be fixed or variable. In an embodiment, the time delay (TD) is a function of the adaptive thresholds ($AT_l$, $AT_u$) 1242. In an embodiment, the time delay (TD) is zero when the lower adaptive threshold ($AT_l$) 1242 is at the second lower limit ($L_2$) 1203 or when the upper adaptive alarm threshold $AT_u$ 1242 is at the second upper limit ($U_2$) 1205.

As shown in FIG. 12B, a baseline processor 1220 embodiment has a sliding window 1250, an over-bias calculator 1260, an under-bias calculator 1265, trend calculators 1270 and response limiters 1280. The sliding window 1250 inputs the parameter 1201 and outputs a time segment 1252 of the parameter 1201. In an embodiment, each window incorporates a five minute span of parameter 1201 values.

Also shown in FIG. 12B, the over-bias calculator 1260 advantageously provides an upward shift in the lower baseline ($B_l$) 1282 for an additional margin of error over missed lower true alarms. That is, a lower baseline ($B_l$) 1282 is generated that tracks a higher-than-average range of parameter values, effectively raising the lower adaptive threshold $AT_l$ slightly above a threshold calculated based upon a true parameter average. In an embodiment, the over-bias calculator 1260 rejects a lower range of parameter values from each time segment 1252 of the sliding window 1250 so as to generate an over-biased time segment 1262.

Further shown in FIG. 12B, the under-bias calculator 1265 advantageously provides a downward shift in the upper baseline ($B_u$) 1287 for an additional margin of error over missed upper true alarms. That is, an upper baseline ($B_u$) 1287 is generated that tracks a lower-than-average range of parameter values, effectively lowering the upper adaptive threshold $AT_u$ slightly below a threshold calculated based upon a true parameter average. In an embodiment, the under-bias calculator 1267 rejects an upper range of parameter values from each time segment 1252 of the sliding window 1250 so as to generate an under-biased time segment 1267.

Additionally shown in FIG. 12B, the trend calculator 1270 outputs an over-biased trend 1272 of the remaining higher range of parameter values in each over-biased segment 1262. Further, the trend calculator 1270 outputs an under-biased trend 1277 of the remaining lower range of parameter values in each under-biased segment 1267. In an embodiment, the biased trends 1272, 1277 are each an average of the values in the corresponding biased time segments 1262, 1267. In other embodiments, the biased trends 1272, 1277 are each a median or mode of the values in the corresponding biased time segments 1262, 1267. The response limiter 1280 advantageously limits the extent to which the baseline 1222 outputs track the biased trends 1272, 1277. Accordingly, the baseline 1222 outputs track only relatively longer-lived transitions of the parameter 1201, but do not track (and hence mask) physiologically significant parameter events. In an embodiment, the response limiter 1280 has a low pass transfer function. In an embodiment, the response limiter 1280 is a slew rate limiter.

Figure 13A:
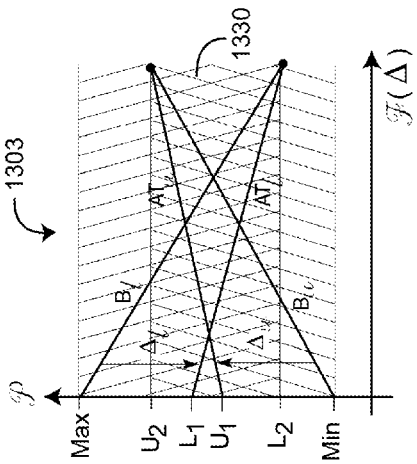
FIGS. 13A-E are physiological parameter versus delta space graphs illustrating a lower-limit adaptive threshold, an upper-limit adaptive threshold, and a combined lower- and upper-limit adaptive threshold in various delta spaces.

FIGS. 13A-E illustrate parameter (P) operating ranges and ideal ranges in view of both lower and upper parameter limits. As shown in FIG. 13A, as the baseline ($B_l$) 1317 decreases (increases) the adaptive threshold ($AT_l$) 1318 monotonically decreases (increases) between $L_1$ and $L_2$. Further, as the baseline ($B_l$) 1317 decreases (increases) the delta ($\Delta_l$) 1319 difference between the baseline ($B_l$) 1317 and the adaptive threshold ($AT_l$) 1318 monotonically decreases (increases) between Max–$L_1$ and 0.

Figure 13B:
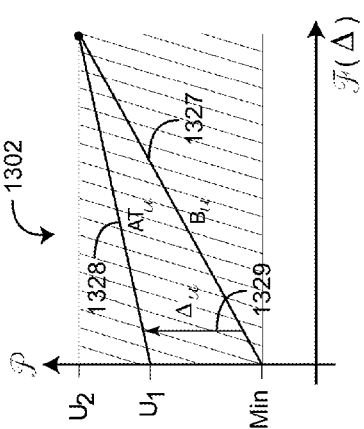

As shown in FIG. 13B, as the baseline ($B_u$) 1327 increases (decreases) the adaptive threshold ($AT_u$) 1328 monotonically increases (decreases) between $U_1$ and $U_2$. Further, as the baseline ($B_u$) 1327 increases (decreases) the delta ($\Delta_u$) 1329 difference between the adaptive threshold ($AT_u$) 1328 and the baseline ($B_u$) 1327 monotonically decreases (increases) between Min–$U_1$ and 0.

Figure 13C:
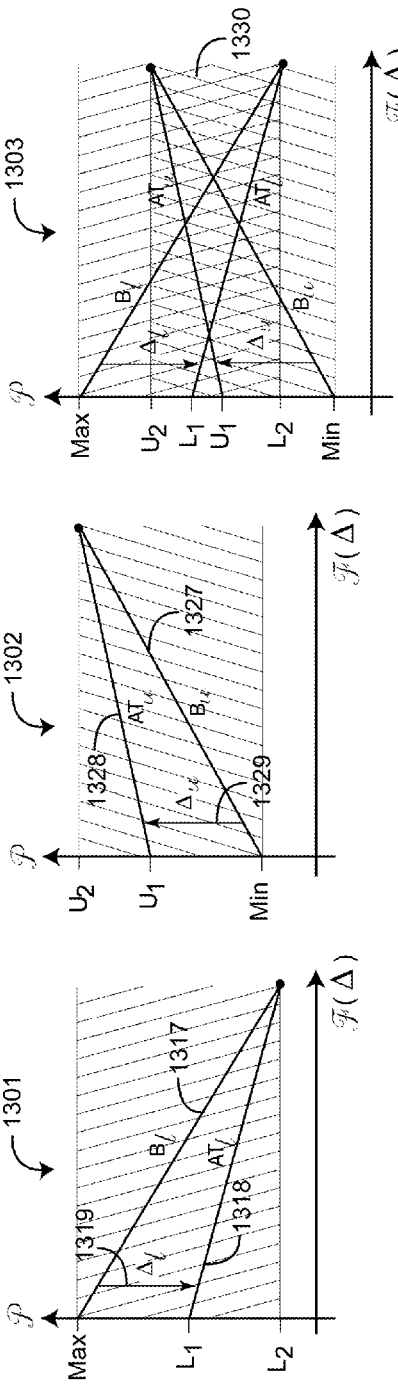

As shown in FIG. 13C, combining FIGS. 13A-B, the parameter (P) operating range is bounded by the overlapping regions of 13A and 13B 1330 having an upper bound of $U_2$ and a lower bound of $L_2$. In particular, $L_1$, $L_2$ are the upper and lower limits of the lower adaptive alarm threshold $AT_l$; and $U_2$, $U_1$ are the upper and lower limits of the upper adaptive alarm threshold $AT_u$.

Figure 13D:
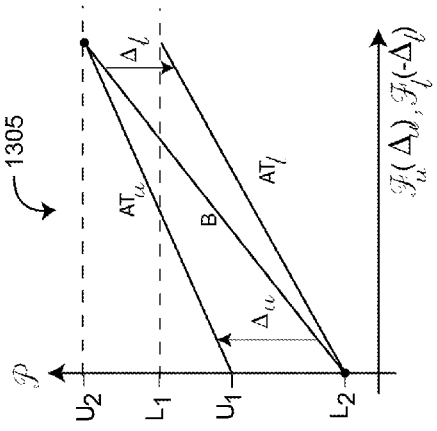
Figure 13E:
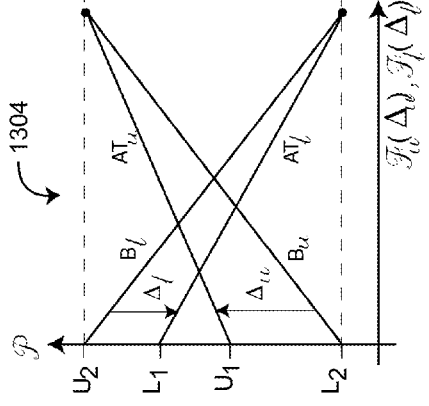

FIG. 13D illustrates parameter (P) versus the overlapping independent delta domains $F_u$, $F_l$ for upper and lower baselines $B_u$, $B_l$; adaptive thresholds $AT_u$, $AT_l$ and deltas $\Delta_u$, $\Delta_l$, based upon FIGS. 13A-C. FIG. 13E illustrates parameter (P) versus the overlapping independent delta domains $F_u$, $F_l$ (reversed); for upper and lower baselines $B_u$, $B_l$; adaptive thresholds $AT_u$, $AT_l$ and deltas $\Delta_u$, $\Delta_l$.

As shown in FIG. 13E, the equations for bi-lateral adaptive thresholds are:

$$\Delta_u = -\left(\frac{U_1 - L_2}{U_2 - L_2}\right)(B - L_2) + (U_1 - L_2) \qquad (9)$$

$$AT_u = B + \Delta_u \qquad (10)$$

where $\Delta_u = U_1 - L_2$ @ $B = L_2$; and $\Delta_u = 0$ @ $B = U_2$; and where $AT_u = U_1$ @ $B = L_2$; and $AT_u = U_2$ @ $B = U_2$.
Further:

$$\Delta_l = \left(\frac{U_2 - L_1}{U_2 - L_2}\right)(B - L_2) \qquad (11)$$

$$AT_l = B - \Delta_l \qquad (12)$$

where $\Delta_l = U_2 - L_1$ @ $B = U_2$; and $\Delta_l = 0$ @ $B = L_2$; and where $AT_l = L_1$ @ $B = U_2$; $AT_l = L_2$ @ $B = L_2$.

Although shown as a linear relationship, in general:

$$\Delta_l = f_1(B); \Delta_u = f_2(B)$$

That is, $\Delta_l$ and $\Delta_u$ can each be a linear function of B, a non-linear function of B or a piecewise linear function of B, to name a few, in a manner similar to that described with respect to FIGS. 5B and 10B, above.

Figure 14:
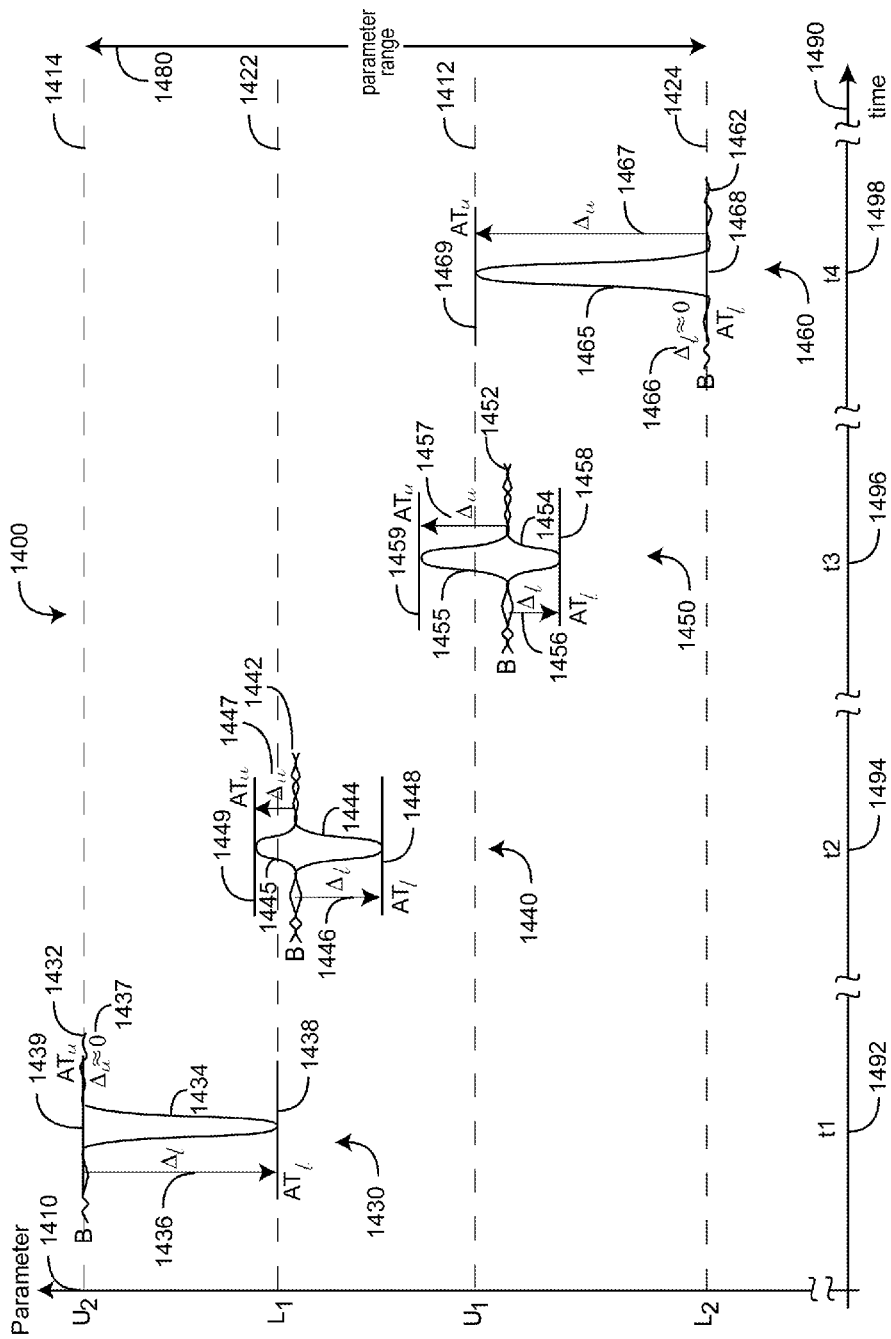
FIG. 14 is an exemplar graph of a physiological parameter versus time illustrating an adaptive alarm system having both lower and upper alarm limits.

FIGS. 14A-B illustrate the operational characteristics an adaptive alarm system 1200 (FIGS. 12A-B) having upper limits $U_1$, $U_2$ 1412, 1414 and lower limits $L_1$, $L_2$ 1422, 1424. An alarm 1212 (FIG. 12A) output is responsive to a baseline (B) 1432, 1442, 1452, 1462; an upper delta ($\Delta_u$) 1437, 1447, 1457, 1467; and a corresponding upper adaptive threshold ($AT_u$) 1439, 1449, 1459, 1469, according to EQS. 9-10, above. Further, the alarm 1212 (FIG. 12A) output is responsive to a lower delta ($\Delta_l$) 1436, 1446, 1456, 1466 and a corresponding lower adaptive threshold ($AT_l$) 1438, 1448, 1458, 1468, according to EQS. 11-12, above.

As shown in FIGS. 14A-B, a physiological parameter 1410 is graphed versus time 1490 for various time segments $t_1$, $t_2$, $t_3$, $t_4$ 1492-1498. The parameter range (PR) 1480 is:

$$PR = U_2 - L_2 \quad (13)$$

the lower adaptive threshold $AT_l$ range is:

$$ATR_l = L_1 - L_2 \quad (14)$$

the upper adaptive threshold $AT_U$ range is:

$$ATR_l = U_2 - U_1 \quad (15)$$

As shown in FIG. 14A, during a first time period $t_1$ 1492, a parameter segment 1430 has a baseline (B) 1432 at about $U_2$ 1414. As such, $\Delta_l$ 1436=$U_2$-$L_1$; $\Delta_u$ 1437=0; $AT_l$ 1438=$L_1$; $AT_u$ 1439=$U_2$. Accordingly, a negative transient 1434 having a size less than $U_2$-$L_1$ does not trigger an alarm.

Also shown in FIG. 14A, during a second time period $t_2$ 1494, a parameter segment 1440 has a baseline (B) 1442 less than $U_2$. As such, $\Delta_l$ 1446 is less than $U_1$-$L_1$ and the adaptive threshold ($AT_u$) 1447 is between $U_1$ and $U_2$. Accordingly, a smaller negative transient 1444 will trigger the alarm as compared to the negative transient 1434 in the first time segment 1430.

Further shown in FIG. 14A, during a third time period $t_3$ 1496, a parameter segment 1450 has a baseline (B) 1452 less than $U_1$ 1412. As such, a smaller negative transient 1454 will trigger the alarm as compared to the negative transient 1444 in the second time segment 1440. However, a larger positive transient 1455 is needed to trigger the alarm as compared to the positive transient 1445 in the second time segment 1440.

Additionally shown in FIG. 14A, during a fourth time period $t_4$ 1460, a parameter segment 1460 has a baseline (B) 1462 at about $L_2$ 1424. As such, $\Delta_l$ 1466=0; $\Delta_u$ 1467=$U_1$-$L_2$; $AT_l$ 1468=$L_2$; $AT_u$ 1469=$U_1$. Accordingly, a positive transient 1465 having a size less than $U_1$-$L_2$ does not trigger an alarm.

An adaptive alarm system has been disclosed in detail in connection with various embodiments. These embodiments are disclosed by way of examples only and are not to limit the scope of the claims that follow. One of ordinary skill in the art will appreciate many variations and modifications.

What is claimed is:

1. A system for reducing electronic alarms in a medical patient monitoring system, the system comprising:
    an optical sensor configured to transmit optical radiation into a tissue site of a patient and detect attenuated optical radiation indicative of at least one physiological parameter of a patient; and
    one or more hardware processors in electronic communication with the optical sensor, the one or more hardware processors configured to:
        measure oxygen saturation values of a patient over a first period of time;
        determine if at least one oxygen saturation value obtained over the first period of time exceeds a first alarm threshold;
        determine whether a first alarm should be triggered based on the determination that the at least one oxygen saturation value obtained over the first period of time exceeds the first alarm threshold;
        determine a second alarm threshold to be applied during a second period of time subsequent to the first period of time, the second alarm threshold replacing the first alarm threshold, the second alarm threshold being determined by:
            comparing at least a first oxygen saturation value obtained during the first time period with a lower limit associated with oxygen saturation; and
            computing a second alarm threshold based on the comparison where the second alarm threshold is computed to be at a value less than the at least first oxygen saturation value and greater than the lower limit and at an offset from the first oxygen saturation value, wherein the offset is configured to diminish as a difference between the at least first oxygen saturation value and the lower limit diminishes;
        measure oxygen saturation values of a patient over the second period of time to determine at least a second oxygen saturation value; and
        determine whether a second alarm should be triggered by determining if at least one oxygen saturation value obtained during the second period of time exceeds the second alarm threshold and triggering an alarm if it is determined the second alarm should be triggered.

2. The system of claim 1, wherein the one or more hardware processors are configured to calculate a first baseline measurement from the measured oxygen saturation values over the first period of time and wherein the at least one oxygen saturation value obtained during the first period of time corresponds to the first baseline measurement.

3. The system of claim 2, wherein the one or more hardware processors are configured to calculate a second baseline measurement from the measured oxygen saturation values over the second period of time and wherein the at least one oxygen saturation value obtained during the second period of time corresponds to the second baseline measurement.

4. The system of claim 1, wherein the lower limit is predefined and corresponds to a minimum parameter value for oxygen saturation.

5. The system of claim 1, wherein the one or more hardware processors are further configured to wait for a time delay prior to the triggering of the second alarm, and wherein the time delay is a function of the second alarm threshold.

6. The system of claim 5, wherein the time delay decreases as the difference between the at least first oxygen saturation value and the lower limit diminishes.

7. The system of claim 1, wherein the first alarm threshold is predetermined.

8. A system for reducing electronic alarms in a medical patient monitoring system including a pulse oximeter in communication with an optical sensor, the system comprising one or more hardware processors configured to:
    measure oxygen saturation values of a patient over a first period of time;
    determine if at least one oxygen saturation value obtained over the first period of time exceeds a first alarm threshold;
    determine whether a first alarm should be triggered based on the determination that the at least one oxygen saturation value obtained over the first period of time exceeds the first alarm threshold;
    compare at least a first oxygen saturation value obtained during the first time period with a lower limit associated with oxygen saturation;
    compute a second alarm threshold based on the comparison;

determine a time delay based on the computed second alarm threshold, wherein the time delay approaches zero as the first oxygen saturation value approaches the lower limit;

measure oxygen saturation values of a patient over the second period of time to determine at least a second oxygen saturation value; and determine whether a second alarm should be triggered by determining if at least one oxygen saturation value obtained during the second period of time exceeds the second alarm threshold for the time delay and triggering an alarm if it is determined the second alarm should be triggered.

9. The system of claim 8, wherein the first alarm threshold is predetermined.

10. The system of claim 8, wherein the lower limit is predefined and corresponds to a minimum parameter value for oxygen saturation.

11. The system of claim 8, where the second alarm threshold is computed to be at a value less than the at least first oxygen saturation value and greater than the lower limit and at an offset from the first oxygen saturation value, wherein the offset is configured to diminish as a difference between the at least first oxygen saturation value and the lower limit diminishes.

12. An electronic method for reducing electronic alarms in a medical patient monitoring system, the electronic method comprising:

measuring oxygen saturation values of a patient over a first period of time;

determining if at least one oxygen saturation value determined over the first period of time exceeds a first alarm threshold;

determining whether a first alarm should be triggered based on the determination that at least one oxygen saturation value obtained during the first period of time exceeds the first alarm threshold;

comparing at least a first oxygen saturation value obtained during the first time period with a lower limit associated with oxygen saturation;

computing the second alarm threshold based on the comparison where the second alarm threshold is computed to be at a value less than the at least first oxygen saturation value and greater than the lower limit and at an offset from the first oxygen saturation value, wherein the offset is configured to diminish as a difference between the at least first oxygen saturation value and the lower limit diminishes and wherein the second alarm threshold is configured to be applied during a second period of time subsequent to the first period of time, the second alarm threshold replacing the first alarm threshold;

measuring oxygen saturation values of a patient over the second period of time to determine at least a second oxygen saturation value; and determining whether a second alarm should be triggered by determining if at least one oxygen saturation value obtained during the second period of time exceeds the second alarm threshold and triggering an alarm if it is determined the second alarm should be triggered.

13. The electronic method of claim 12, wherein the one or more hardware processors are configured to calculate a first baseline measurement from the measured oxygen saturation values over the first period of time and wherein the at least one oxygen saturation value obtained during the first period of time corresponds to the first baseline measurement.

14. The electronic method of claim 13, wherein the one or more hardware processors are configured to calculate a second baseline measurement from the measured oxygen saturation values over the second period of time and wherein the at least one oxygen saturation value obtained during the second period of time corresponds to the second baseline measurement.

15. The electronic method of claim 12, wherein the lower limit is predefined and corresponds to a minimum parameter value for oxygen saturation.

16. The electronic method of claim 12, wherein the one or more hardware processors are further configured to wait for a time delay prior to the triggering of the second alarm, and wherein the time delay is a function of the second alarm threshold.

17. The electronic method of claim 16, wherein the time delay decreases as the difference between the at least first oxygen saturation value and the lower limit diminishes.

18. The electronic method of claim 12, wherein the first alarm threshold is predetermined.

* * * * *